(12) United States Patent  (10) Patent No.: US 8,951,563 B2
Mor et al.  (45) Date of Patent: Feb. 10, 2015

(54) ANTIBIOTIC DRUG DELIVERY AND POTENTIATION

(75) Inventors: Amram Mor, Nesher (IL); Richard M. Epand, Hamilton (CA); Raquel F. Epand, Hamilton (CA); Brigitte Papahadjopoulos-Sternberg, San Francisco, CA (US)

(73) Assignee: Technion Research & Development Foundation Limited, Haifa (IL)

( * ) Notice: Subject to any disclaimer, the term of this patent is extended or adjusted under 35 U.S.C. 154(b) by 43 days.

(21) Appl. No.: 13/389,008

(22) PCT Filed: Aug. 5, 2010

(86) PCT No.: PCT/IL2010/000638
§ 371 (c)(1),
(2), (4) Date: May 22, 2012

(87) PCT Pub. No.: WO2011/016043
PCT Pub. Date: Feb. 10, 2011

(65) Prior Publication Data
US 2012/0237562 A1 Sep. 20, 2012

Related U.S. Application Data

(60) Provisional application No. 61/231,709, filed on Aug. 6, 2009.

(51) Int. Cl.
*A61K 9/14* (2006.01)
(52) U.S. Cl.
USPC .................................................. 424/489
(58) Field of Classification Search
None
See application file for complete search history.

(56) References Cited

U.S. PATENT DOCUMENTS

| 5,846,955 | A | 12/1998 | Pidgeon et al. |
| 7,351,688 | B2 * | 4/2008 | Balasubramanian et al. .................. 424/278.1 |
| 2004/0092727 | A1 | 5/2004 | Jin |
| 2007/0032428 | A1 | 2/2007 | Mor et al. |

FOREIGN PATENT DOCUMENTS

| WO | WO 98/25953 | 6/1998 |
| WO | WO 2006/035431 | 4/2006 |
| WO | WO 2008/132738 | 11/2008 |

(Continued)

OTHER PUBLICATIONS

International Preliminary Report on Patentability Dated Feb. 16, 2012 From the International Bureau of WIPO Re. Application No. PCT/IL2010/000638.

(Continued)

*Primary Examiner* — Paul Dickinson

(57) ABSTRACT

Disclosed are compositions-of-matter comprising polymer-mediated cochleates, which are formed from a calcium-free mixture of a wide variety of phospholipids that are atypical for forming cochleates. Further disclosed are compositions-of-matter comprising these cochleates which co-encapsulate another bioactive agent. The polymer mediating the formation of these cochleates exhibits a plurality of positively charged amino acid residues and omega-amino-fatty acid moieties, and may further exhibit antimicrobial, anticancerous and drug-potentiating activity. Further disclosed are pharmaceutical compositions and methods using the compositions-of-matter disclosed herein, and processes of preparing same.

31 Claims, 9 Drawing Sheets

(56) References Cited

FOREIGN PATENT DOCUMENTS

| WO | WO 2009/090648 | 7/2009 |
|----|----------------|--------|
| WO | WO 2011/016043 | 2/2011 |

OTHER PUBLICATIONS

Official Action Dated Apr. 19, 2013 From the US Patent and Trademark Office Re. U.S. Appl. No. 12/812,965.

International Preliminary Report on Patentability Dated Jul. 29, 2010 From the International Searching Authority Re.: Application No. PCT/IL2009/000063.

International Search Report and the Written Opinion Dated Oct. 11, 2011 From the International Searching Authority Re.: Application No. PCT/IL2010/000638.

International Search Report and the Written Opinion Dated Sep. 16, 2009 From the International Searching Authority Re.: Application No. PCT/IL2009/000063.

Radzishevsky et al. "Improved Antimicrobial Peptides Based on Acyl-Lysine Oligomers", Nature Biotechnology, XP002544172, 25(6): 657-659, 2007.

Radzishevsky et al. "Structure-Activity Relationships of Antibacterial Acyl-Lysine Oligomers", Chemistry & Biology, XP022613218, 15(4): 354-362, Apr. 21, 2008. Abstract.

Syed et al. "Cochleates Bridged by Drug Molecules", International Journal of Pharmaceutics, 363: 118-125, 2008.

Restriction Official Action Dated Oct. 5, 2012 From the US Patent and Trademark Office Re. U.S. Appl. No. 12/812,965.

Official Action Dated Dec. 11, 2013 From the US Patent and Trademark Office Re. U.S. Appl. No. 12/812,965.

\* cited by examiner

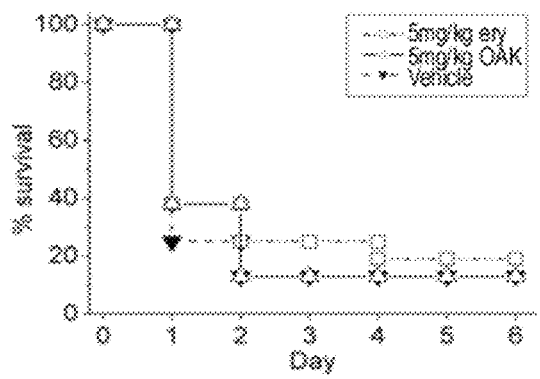 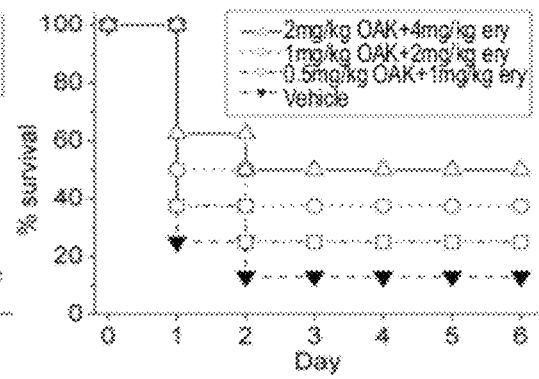
FIG. 5A  FIG. 5B
 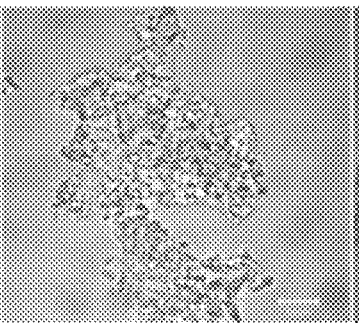 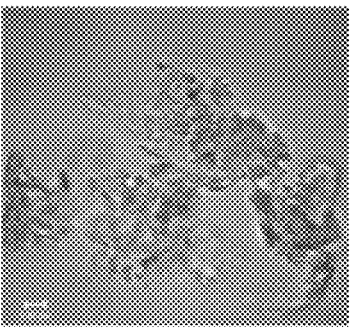
FIG. 6A  FIG. 6B  FIG. 6C
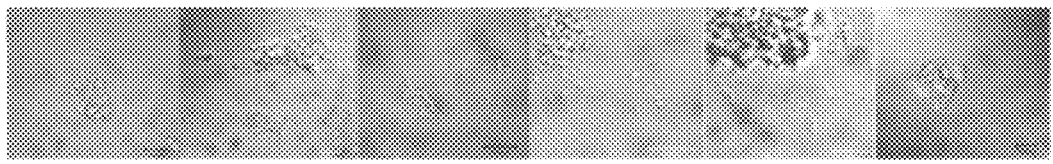
FIG. 7A  FIG. 7B  FIG. 7C  FIG. 7D  FIG. 7E  FIG. 7F
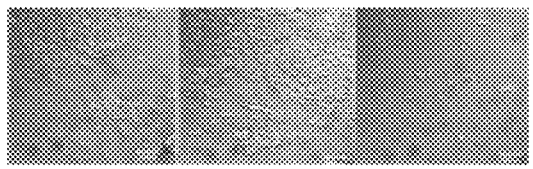
FIG. 7G  FIG. 7H  FIG. 7I

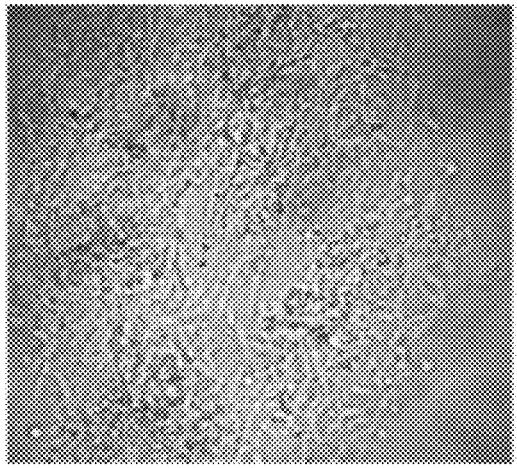 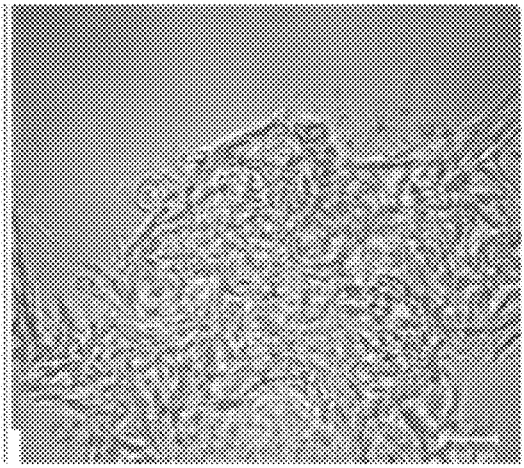
FIG. 8A  FIG. 8B
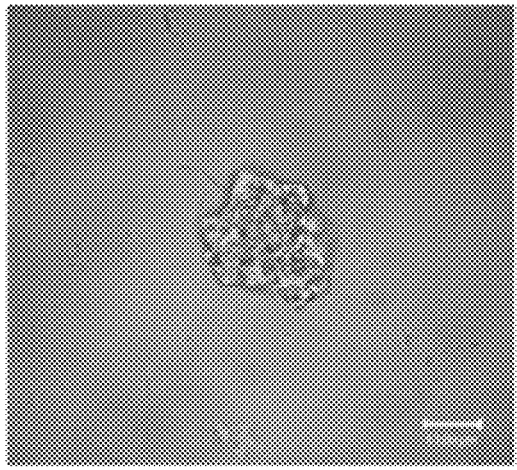 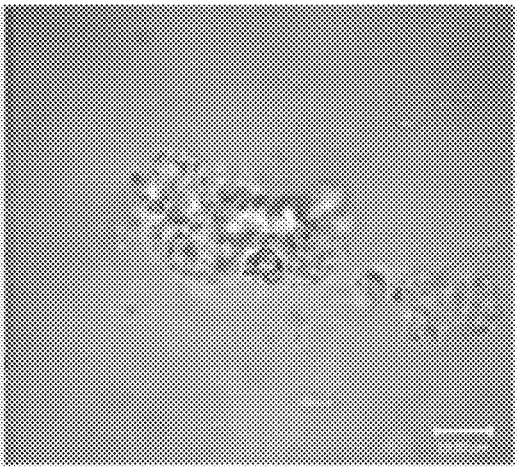
FIG. 8C  FIG. 8D

```
                         SEQUENCE LISTING

<160> NUMBER OF SEQ ID NOS: 9

<210> SEQ ID NO 1
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid

<400> SEQUENCE: 1

Lys Xaa Lys Xaa Lys Xaa Lys Xaa Lys Xaa Lys
1               5                   10

<210> SEQ ID NO 2
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
```

```
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid

<400> SEQUENCE: 2

Lys Xaa Lys Xaa Lys Xaa Lys Xaa Lys Xaa Lys Xaa Lys
1               5                   10

<210> SEQ ID NO 3
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid
<220> FEATURE:
<221> NAME/KEY: misc_feature
<222> LOCATION: (14)..(14)
<223> OTHER INFORMATION: Omega-amino-8 carbon fatty acid

<400> SEQUENCE: 3

Lys Xaa Lys Xaa Lys Xaa Lys Xaa Lys Xaa Lys Xaa Lys Xaa Lys
1               5                   10                  15

<210> SEQ ID NO 4
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
```

```
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid
<220> FEATURE:
<221> NAME/KEY: misc_feature
<222> LOCATION: (14)..(14)
<223> OTHER INFORMATION: Omega-amino-8 carbon fatty acid
<220> FEATURE:
<221> NAME/KEY: misc_feature
<222> LOCATION: (16)..(16)
<223> OTHER INFORMATION: Omega-amino-8 carbon fatty acid

<400> SEQUENCE: 4

Lys Xaa Lys Xaa Lys Xaa Lys Xaa Lys Xaa Lys Xaa Lys Xaa Lys Xaa
1               5                   10                  15

Lys

<210> SEQ ID NO 5
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
```

```
<221> NAME/KEY: misc_feature
<222> LOCATION: (12)..(12)
<223> OTHER INFORMATION: Omega-amino-8 carbon fatty acid
<220> FEATURE:
<221> NAME/KEY: misc_feature
<222> LOCATION: (14)..(14)
<223> OTHER INFORMATION: Omega-amino-8 carbon fatty acid
<220> FEATURE:
<221> NAME/KEY: misc_feature
<222> LOCATION: (16)..(16)
<223> OTHER INFORMATION: Omega-amino-8 carbon fatty acid
<220> FEATURE:
<221> NAME/KEY: misc_feature
<222> LOCATION: (18)..(18)
<223> OTHER INFORMATION: Omega-amino-8 carbon fatty acid

<400> SEQUENCE: 5

Lys Xaa Lys Xaa Lys Xaa Lys Xaa Lys Xaa Lys Xaa Lys Xaa Lys Xaa
1               5                   10                  15

Lys Xaa Lys

<210> SEQ ID NO 6
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid
<220> FEATURE:
<221> NAME/KEY: misc_feature
<222> LOCATION: (14)..(14)
<223> OTHER INFORMATION: Omega-amino-8 carbon fatty acid
<220> FEATURE:
<221> NAME/KEY: misc_feature
<222> LOCATION: (16)..(16)
<223> OTHER INFORMATION: Omega-amino-8 carbon fatty acid
<220> FEATURE:
<221> NAME/KEY: misc_feature
<222> LOCATION: (18)..(18)
<223> OTHER INFORMATION: Omega-amino-8 carbon fatty acid
<220> FEATURE:
<221> NAME/KEY: misc_feature
<222> LOCATION: (20)..(20)
<223> OTHER INFORMATION: Omega-amino-8 carbon fatty acid
<220> FEATURE:
```

```
<221> NAME/KEY: misc_feature
<222> LOCATION: (22)..(22)
<223> OTHER INFORMATION: Omega-amino-8 carbon fatty acid

<400> SEQUENCE: 6

Lys Xaa Lys Xaa Lys Xaa Lys Xaa Lys Xaa Lys Xaa Lys Xaa Lys Xaa
1               5                   10                  15

Lys Xaa Lys Xaa Lys Xaa Lys
            20

<210> SEQ ID NO 7
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid
<220> FEATURE:
<221> NAME/KEY: misc_feature
<222> LOCATION: (12)..(12)
<223> OTHER INFORMATION: Omega-amino-4 carbon fatty acid
<220> FEATURE:
<221> NAME/KEY: misc_feature
<222> LOCATION: (14)..(14)
<223> OTHER INFORMATION: Omega-amino-4 carbon fatty acid

<400> SEQUENCE: 7

Lys Xaa Lys Xaa Lys Xaa Lys Xaa Lys Xaa Lys Xaa Lys Xaa Lys
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-8 carbon fatty acid
```

```
<220> FEATURE:
<221> NAME/KEY: misc_feature
<222> LOCATION: (5)..(5)
<223> OTHER INFORMATION: Omega-amino-8 carbon fatty acid
<220> FEATURE:
<221> NAME/KEY: misc_feature
<222> LOCATION: (7)..(7)
<223> OTHER INFORMATION: Omega-amino-8 carbon fatty acid
<220> FEATURE:
<221> NAME/KEY: misc_feature
<222> LOCATION: (9)..(9)
<223> OTHER INFORMATION: Omega-amino-8 carbon fatty acid
<220> FEATURE:
<221> NAME/KEY: misc_feature
<222> LOCATION: (11)..(11)
<223> OTHER INFORMATION: Omega-amino-8 carbon fatty acid
<220> FEATURE:
<221> NAME/KEY: misc_feature
<222> LOCATION: (13)..(13)
<223> OTHER INFORMATION: Omega-amino-8 carbon fatty acid
<220> FEATURE:
<221> NAME/KEY: misc_feature
<222> LOCATION: (15)..(15)
<223> OTHER INFORMATION: Omega-amino-8 carbon fatty acid

<400> SEQUENCE: 8

Xaa Lys Xaa Lys Xaa Lys Xaa Lys Xaa Lys Xaa Lys Xaa Lys Xaa Lys
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid
<220> FEATURE:
<221> NAME/KEY: misc_feature
<222> LOCATION: (8)..(8)
<223> OTHER INFORMATION: Omega-amino-12 carbon fatty acid
<220> FEATURE:
<221> NAME/KEY: misc_feature
<222> LOCATION: (10)..(10)
<223> OTHER INFORMATION: Omega-amino-12 carbon fatty acid
<220> FEATURE:
<221> NAME/KEY: misc_feature
<222> LOCATION: (12)..(12)
<223> OTHER INFORMATION: Omega-amino-12 carbon fatty acid
<220> FEATURE:
<221> NAME/KEY: misc_feature
<222> LOCATION: (14)..(14)
<223> OTHER INFORMATION: Omega-amino-12 carbon fatty acid

<400> SEQUENCE: 9

Lys Xaa Lys Xaa Lys Xaa Lys Xaa Lys Xaa Lys Xaa Lys Xaa Lys
1               5                   10                  15
```

ANTIBIOTIC DRUG DELIVERY AND POTENTIATION

RELATED APPLICATIONS

This application is a National Phase of PCT Patent Application No. PCT/IL2010/000638 having International filing date of Aug. 5, 2010, which claims the benefit of priority of U.S. Provisional Patent Application No. 61/231,709 filed on Aug. 6, 2009. The contents of the above applications are all incorporated herein by reference.

FIELD AND BACKGROUND OF THE INVENTION

The present invention, in some embodiments thereof, relates to pharmaceuticals and more particularly, but not exclusively, to novel cochleate-based systems and uses thereof as drug delivery vehicles in the treatment of medical conditions such as, for example, conditions associated with antibiotic-resistant pathogenic microorganisms.

Antibiotic resistance represents a worldwide health problem where treatment failure of an ever increasing number of pathogens is intimately associated with severe outcomes such as increased mortality and morbidity. This grave state of events is largely due to a multitude of biochemical and genetic strategies that bacteria have developed to neutralize the threats imposed by antibiotics. Resistance acquirement by bacteria can be divided into four main aspects: i) direct inactivation by hydrolysis, acylation or oxidation; ii) target modification that reduce sensitivity to antibiotics (e.g. ribosome structure; iii) target bypass, i.e., bacteria become refractory to specific antibiotics by bypassing their inactivation mechanism; iv) efflux pumps, which reduce intracellular drug concentration due to their active export out of the cell. While efflux pumps may induce relatively low level resistance to many classes of antibiotics, especially macrolides, tetracyclines, and fluoroquinolones, which inhibit biosynthesis and therefore must accumulate inside bacteria, they contribute significantly to multidrug resistance (MDR).

Host derived cationic antimicrobial peptides (AMPs) and their synthetic mimics are widely regarded as a potential source of future therapeutic agents against a broad range of pathogens. Various AMPs have shown an ability to act synergistically with conventional antibiotics such as β-lactams, macrolides, tetracycline, ciprofloxacin and rifampin, thereby sensitizing antibiotic-resistant bacteria. Conversely, antibiotics may sensitize AMP-resistant bacteria although, in all cases, the molecular basis for these phenomena was not addressed experimentally. While peptide-based antimicrobials represent a class of promising agents in fighting bacterial resistance to antibiotics, difficult challenges need to be overcome towards their eventual use in therapeutics, including the need to improve bioavailability, toxicity and production costs. Another concern for therapeutic uses of AMPs pertains to the emergence of extreme resistance phenomena to the host defense system. Bacteria may sense AMPs via a variety of two-component sensor/regulator systems (TCSs, e.g., PhoPQ or PmrAB), that regulate specific gene expression leading to greater stability of the outer membrane and adapting bacteria for survival. As some AMPs were found to activate one or more TCSs, concern stems from general use of host defense peptides which may provoke the evolution of resistance that will compromise our natural defenses against infection. Hence, synthetic AMP-mimics that retain antibacterial activity but lack the ability to activate PhoQ or its orthologs would represent preferable therapeutics.

A wide range of strategies were put forward in the attempt to alleviate one or more of these shortcomings through chemical mimics that reproduce the AMPs most critical biophysical characteristics in unnatural, sequence-specific oligomers.

U.S. Pat. No. 7,504,381, WO 2006/035431, WO 2008/132738, WO 2009/090648 and U.S. Patent Application Nos. 20070032428 and 20100120671, by one of the present inventors, which are incorporated herein by reference as if fully set forth herein, teach a novel class of peptidomimetic antimicrobial and/or anticancerous polymers. These antimicrobial and/or anticancerous polymers, also referred to as oligo-acyl-lysyl (OAK) polymers, are composed of hydrophobic moieties and amino acids, and maintain three key attributes of AMPs: a flexible structure, an amphiphatic character and a net positive charge. As presented in these patent applications, these antimicrobial polymers are composed of positively charged amino acid residues, such as lysine, and non-amino acid hydrophobic moieties, such as ω-amino-fatty acid residues, as well as fatty acid residues, which not only achieve the desired amphiphatic trait and resolve the production and maintenance issues limiting the use of polypeptides as drugs, but also alleviate the severe limitations restricting the administration of polypeptides as drugs.

The aforementioned OAK polymers have been shown to exhibit high and synergistic antimicrobial and/or anticancerous activity, low resistance induction, re-sensitization of antibiotic-resistant pathogens, non-hemolyticity, resistibility to plasma proteases and high affinity to microbial membranes. Hence, the OAK polymer approach appears to offer advantages owing to its simplicity of design which so far generated OAK sequences with selective antimicrobial and antitumor properties both in test tubes and in animal models of disease, while exhibiting a certain potential for addressing problems related to MDR phenomena.

Oral delivery is the most suitable way of administering drugs for most non-hospitalized, non-acute care patients. Drug delivery systems that allow oral delivery improve patient compliance and facilitate treatment outside the hospital, which has a significant impact on healthcare economics. Many drug delivery platforms have emerged and are present in either a preclinical stage or in an advanced clinical trial with the intent of trying to demonstrate efficient oral absorption. In particular, cochleate technology was shown to be effective in the therapeutic oral delivery of the hydrophobic antifungal agent amphotericin B.

Cochleates are roll-like microstructures that consist of a series of lipid bilayers, which are formed as a result of the condensation of small unilamellar negatively charged liposomes. In the presence of calcium, the small phosphatidylserine (PS) liposomes fuse and form large sheets which have hydrophobic surfaces and, in order to minimize their interactions with water, tend to roll-up into the turbinated cylindrical lipid bilayers, or cochleate.

Cochleates were discovered in 1975, and have been used in the 80s and 90s to transport antigens and peptides for vaccine delivery. It was demonstrated that by using a binary phase system, such as two non-miscible hydrogels, cochleates can be formed that display a small mean particle of less than 500 nm. These cochleates were highly suitable for the encapsulation of hydrophobic drugs, such as amphotericin B.

Freeze-fracture electron microscopy reveals a typical cochleate cylinder characterized by the elongated shape and by the tight packed bilayers. Because cochleates contain both hydrophobic and hydrophilic surfaces, they are suitable to encapsulate both hydrophobic drugs like amphotericin B and clofazimine and amphiphathic drugs like doxorubicin. The loading efficacy of the cochleates depends upon the physical chemistry of the drug to encapsulate, whereas the particle size of the drug-cochleate complex depends on the process used to encapsulate. The main components of currently known cochleates are phosphatidylserine (PS) and calcium, two natural compounds. Phosphatidylserine is a constituent of the brain and is sold in health stores as a nutrient supplement.

WO 1996/025942 and WO 1997/030725 disclose cochleates comprising a biologically relevant molecule component, a negatively charged lipid component, and a divalent cation component, wherein the biologically relevant molecule can be a polynucleotide or a polypeptide.

U.S. Pat. No. 6,592,894 discloses a process for producing a small-sized, lipid-based cochleates which are derived from liposomes that are suspended in an aqueous two-phase polymer solution, and treated with positively charged molecules such as Ca2+ or Zn2+, and which may contain biologically relevant molecules.

U.S. Patent Application No. 20040092727 teaches cochleates wherein the agents bridging the lipid bilayer are organic multi-valent cations such as 2,3,5,6-tetraminopyrimidine sulfate.

Syed, U M, et al. [Syed, U M, et al., Int J Pharm, 2008, 363, (1-2):118-125] disclose cochleates which are able to microencapsulate water-soluble cationic drugs or peptides into its inter-lipid bi-layer space. These cochleates were formed through interaction between negatively charged lipids and drugs or peptides, such as poly-L-Lysine, acting as the inter-bi-layer bridges in addition to the presence of $Ca^{2+}$.

SUMMARY OF THE INVENTION

On studying the ability of oligo-acyl-Lysines (OAK polymers) to promote clustering of anionic lipids in mixtures containing zwitterionic and anionic lipids which mimic the cytoplasmic membrane of bacteria, the present inventors have surprisingly uncovered that these polymers are capable of promoting the formation of lipid cochleates (turbinated multilamellar lipid bilayers).

These cochleates have been shown for the first time to form in the absence of divalent cations.

Thus, it was further surprisingly uncovered that these cochleates are obtainable in the presence of these OAK polymers under chemical conditions and in lipid compositions which were not shown as supportive of cochleate formation hitherto.

It was further uncovered that when forming such cochleates in the presence of an OAK polymer as described herein and optionally in the presence of other chemical entities such as classical antibiotic agents, a highly effective drug delivery vehicle is formed. The drug delivery vehicle is such that the polymer is encapsulated in the turbinated lipid bilayer, and optionally another chemical entity such as, for example, an antibiotic agent, is co-encapsulated with the polymer, thereby endowing physical and chemical protection and controlled release environment for the polymer, the bioactive agent or both when introduced into physiological media and surroundings in vivo.

As discussed hereinabove, it has been previously shown that combinations of OAK polymers and other targeted cytotoxic drugs, such as anticancerous and antibiotic drugs, may act in synergy and/or in combination by exhibiting an efficient synergistic cytotoxic effect against cancerous cells and/or by exhibiting re-sensitization of a microorganism to an antibiotic agent (see, WO 2008/132738 and WO 2009/090648 respectively).

It has now been demonstrated that antibiotic drug delivery vehicles prepared with OAK-mediated cochleates, can be used effectively to treat infections caused by pathogenic microorganisms in general, and are particularly effective against pathogenic microorganisms which have already developed resistance to the antibiotic agent. In such antimicrobial delivery system, the OAK polymer has a passive role that drives cochleate formation, and an active role destined to potentiate the co-encapsulated antibiotic by sensitizing bacteria thereto.

Hence, according to an aspect of some embodiments of the present invention, there is provided a composition-of-matter which comprises a cochleate and a polymer encapsulated in the cochleate, wherein the cochleate is formed from a mixture of at least two phospholipids, and the polymer comprises a plurality of positively charged amino acid residues and at least one ω-amino-fatty acid moiety, wherein the ω-amino-fatty acid moiety is covalently linked to at least two amino acid residues via the N-alpha of one amino acid residue and via the C-alpha of the other amino acid residue.

According to some embodiments, the composition-of-matter is substantially devoid of multivalent metal cations (e.g., divalent metal cations such as $Ca^{+2}$).

According to some embodiments of the present invention, a polymer which exhibits a majority of lysine residues in its plurality of positively charged amino acid residues is also referred to as an oligo-acyl-lysyl polymer, or OAK. However, in the context of embodiments of the present invention, the terms "polymer" and "OAK" are used interchangeably.

According to some embodiments, the net positive charge of the polymer ranges from 6 to 12 or from 8 to 10.

According to some embodiments, the polymer comprises from 4 to 12 $NC_{4-12}K$ combined units, or from 6 to 10 $NC_{4-12}K$ combined units.

According to some embodiments, the N-terminus unit of the polymer is selected from the group consisting of a lysine residue having a $NC_{10-16}$ fatty acid moiety attached thereto and a lysine residue having a $C_{10-16}$ fatty acid moiety attached thereto.

According to some embodiments, the $NC_{10-16}$ fatty acid moiety is an $NC_{12}$ fatty acid moiety.

According to some embodiments, the $C_{10-16}$ fatty acid moiety is a $C_{12}$ fatty acid moiety.

According to some embodiments, each of the ω-amino fatty acid moieties is independently selected from the group consisting of 4-amino-butyric acid, 6-amino-caproic acid, 8-amino-caprylic acid, 10-amino-capric acid and 12-amino-lauric acid.

According to some embodiments, each of the ω-amino fatty acid moieties is independently selected from the group consisting of 6-amino-caproic acid, 8-amino-caprylic acid and 10-amino-capric acid.

According to some embodiments, each of the ω-amino fatty acid moieties is 8-amino caprylic acid.

According to some embodiments, the polymer comprises from 4 to 12 $NC_8K$ combined units, or from 6 to 10 $NC_8K$ combined units.

According to some embodiments, the polymer comprises from 4 to 12 consecutive $NC_{4-12}K$ combined units (4-12$α_{4-12}$), or from 6 to 10 consecutive $NC_{4-12}K$ combined units (6-10$α_{4-12}$).

According to some embodiments, the polymer comprises from 4 to 12 consecutive $NC_8K$ combined units (4-12$α_8$), or from 6 to 10 consecutive $NC_8K$ combined units (6-10$α_8$).

According to some embodiments, the polymer has the general Formula I:

X-W0-[A1-Z1-D1]-W1-[A2-Z2-D2]-W2- . . . [An-Zn-Dn]-Wn-Y         Formula I wherein:

n is an integer from 2 to 50;

A1, A2, . . . , An are each independently the positively charge amino acid residue;

D1, D2, . . . , Dn are each independently the ω-amino-fatty acid moiety or absent, provided that at least one of the D1, D2, . . . , Dn is the ω-amino-fatty acid moiety;

Z1, Z2, ..., Zn and W0, W1, W2, ..., Wn are each independently a linking moiety linking an amino acid residue and a ω-amino-fatty acid moiety, or absent; and X and Y are each independently selected from the group consisting of hydrogen, amine, amide, a positively charged amino acid residue, an ω-amino-fatty acid moiety and a fatty acid moiety, or absent.

According to some embodiments, the polymer is selected from the group consisting of $C_{12}K(NC_8K)_5NH_2$ (SEQ ID NO: 1), $C_{12}K(NC_8K)_6NH_2$ (SEQ ID NO: 2), $C_{12}K(NC_8K)_7NH_2$ (SEQ ID NO: 3), $C_{12}K(NC_8K)_8NH_2$ (SEQ ID NO: 4), $C_{12}K(NC_8K)_9NH_2$ (SEQ ID NO: 5), $C_{12}K(NC_8K)_{11}NH_2$ (SEQ ID NO: 6), $C_{12}K(NC_4K)_7NH_2$ (SEQ ID NO: 7), $NC_{12}K(NC_8K)_7NH_2$ (SEQ ID NO: 8) and $C_{12}K(NC_{12}K)_7NH2$ (SEQ ID NO: 9).

According to some embodiments, the mixture of phospholipids is characterized by a melting temperature higher than 20° C., or higher than 30° C., or higher than 40° C., or higher than 50° C.

According to some embodiments, the mixture of phospholipids is characterized by a melting temperature that ranges from 15° C. to 45° C.

According to some embodiments, each of the phospholipids is independently selected from the group consisting of a zwitterionic phosphatidylcholine, a zwitterionic phosphatidylethanolamine, an anionic phosphatidylglycerol and an anionic diphosphatidylglycerol.

According to some embodiments, at least one of the phospholipids is a zwitterionic phosphatidylethanolamine and at least another phospholipid is an anionic diphosphatidylglycerol.

According to some embodiments, at least one of the two phospholipids in the mixture is selected from the group consisting of POPG, POPE, POPC, DPPE, DOPE, DMPG, DMPE and DMPC, and the other phospholipid in the mixture is selected from the group consisting of TOCL and DOPG.

According to some embodiments, one phospholipid of the two phospholipids is DMPE and the other phospholipid is TOCL.

According to some embodiments, one phospholipid of the two phospholipids is DPPE and the other phospholipid is TOCL.

According to some embodiments, one phospholipid of the two phospholipids is DMPE and the other phospholipid is DOPG.

According to some embodiments, the respective molar ratio of the phospholipids ranges from 1:1 to 9:1, According to some embodiments, the respective molar ratio is 3:1.

According to some embodiments, the mixture comprises DMPE and TOCL at a molar ratio of 3:1.

According to some embodiments, the mixture comprises DPPE and TOCL at a molar ratio of 3:1.

According to some embodiments, the mixture comprises DMPE and DOPG at a molar ratio of 3:1.

According to some embodiments, the phospholipid lipid mixture is essentially devoid of phosphatidylserine.

According to some embodiments, the polymer has an antimicrobial activity.

According to some embodiments, the polymer has an anticancerous activity.

According to some embodiments, the phospholipid mixture and the concentration of the polymer are selected such that a therapeutically effective amount of the polymer is released under physiological conditions.

According to some embodiments, the composition-of-matter presented herein is identified for use in the treatment of a medical condition treatable by the polymer.

According to some embodiments, the composition-of-matter presented herein further includes a bioactive agent co-encapsulated in the cochleate.

According to some embodiments, the mixture and the concentration of the polymer are selected such that a therapeutically effective amount of the bioactive agent is released under physiological conditions.

According to some embodiments, the maximal tolerated dose (MTD) of the polymer encapsulated in the cochleate is higher by at least 2-fold, 3-fold, 4-fold, 8-fold, 12-fold and 20-fold, as compared to a maximal tolerated dose (MTD) of a non-encapsulated form of the polymer.

According to some embodiments, the composition-of-matter presented herein further comprises an antibiotic agent co-encapsulated in the cochleate.

According to some embodiments, the composition-of-matter presented herein is identified for use in treating a medical condition associated with a pathogenic microorganism.

According to some embodiments, the pathogenic microorganism is a resistant pathogenic microorganism.

According to some embodiments, the resistance mechanism of the resistant pathogenic microorganism is substantially an efflux-enhanced drug resistance mechanism.

According to some embodiments, the antibiotic agent is an intracellular-targeting antibiotic agent.

According to some embodiments, the intracellular-targeting antibiotic agent is selected from the group consisting of erythromycin, clarithromycin, tetracycline, rifampicin and ciprofloxacin.

According to some embodiments, the resistant pathogenic microorganism is selected from the group consisting of Gram-negative bacteria such as *E. coli* or Gram-positive bacteria such as *S. aureus*.

According to some embodiments, the composition-of-matter presented herein is identified for use in re-sensitizing the pathogenic microorganism to the antibiotic agent.

According to some embodiments, the bioactive agent is an anticancerous agent.

According to some embodiments, the composition-of-matter presented herein is identified for use in the treatment of cancer.

According to some embodiments, the composition-of-matter presented herein is identified for use in delivering the bioactive agent to a bodily site of a subject in need thereof.

According to another aspect of some embodiments of the present invention, there is provided a pharmaceutical composition which includes the composition-of-matter presented herein and a pharmaceutically acceptable carrier.

According to some embodiments, the pharmaceutical composition is packaged in a packaging material and identified, in or on the packaging material, for use in the treatment of a medical condition treatable by the polymer.

According to some embodiments, the pharmaceutical composition includes a composition-of-matter which further comprises a bioactive agent co-encapsulated in the cochleate.

According to some embodiments, the pharmaceutical composition is packaged in a packaging material and identified, in or on the packaging material, for use in a systemic or local delivery of the bioactive agent to a bodily site of a subject in need thereof.

According to some embodiments, the pharmaceutical composition includes a composition-of-matter which further comprises a bioactive agent which is an anticancerous agent, and the pharmaceutical composition is identified for use in the treatment of cancer.

According to some embodiments, the pharmaceutical composition includes a composition-of-matter which further comprises bioactive agent which is an antibiotic, and the pharmaceutical composition is packaged in a packaging material and identified, in or on the packaging material, for use in treating a medical condition associated with a pathogenic microorganism.

According to some embodiments in the context of the pharmaceutical composition, the pathogenic microorganism is a resistant microorganism, and the pharmaceutical composition is further identified for re-sensitizing the resistant microorganism to the antibiotic agent.

According to some embodiments, the pharmaceutical composition presented herein is formulated for administration via a route selected from the group consisting of oral, intravenous, subcutaneous, intramuscular, intraperitoneal and intrathecal routes.

According to another aspect of some embodiments of the present invention, there is provided a method of treating a medical condition associated with a pathogenic microorganism, which comprises administering to a subject in need thereof a therapeutically effective amount of the composition-of-matter presented herein or the pharmaceutical composition presented herein.

According to some embodiments, the pathogenic microorganism is a resistant microorganism, and the method is for re-sensitizing the microorganism to an antibiotic agent.

According to another aspect of some embodiments of the present invention, there is provided a method of delivering a bioactive agent to a bodily site of a subject in need thereof, the method comprising administering to the subject the composition-of-matter presented herein.

According to another aspect of some embodiments of the present invention, there is provided a use of the composition-of-matter presented herein for the preparation of a medicament for the treating a medical condition in a subject, as described herein.

According to another aspect of some embodiments of the present invention, there is provided a process of preparing the composition-of-matter presented herein, the process comprising:

providing a dehydrated film of the mixture; and
hydrating the film with an aqueous solution of the polymer according to some embodiments of the present invention, thereby obtaining the composition-of-matter presented herein.

According to some embodiments in the context of a process of preparing the composition-of-matter, the phospholipid mixture is essentially devoid of phosphatidylserine.

According to some embodiments, the process of preparing the composition-of-matter is effected essentially in the absence of a multivalent metal cation.

According to another aspect of some embodiments of the present invention, there is provided a polymer having the formula C12K(NC8K)11NH2 (SEQ ID NO: 6).

As used herein the term "about" refers to ±10%.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "treating" and "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the composite being administered which will relieve to some extent one or more of the symptoms of the condition being treated.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIGS. 2A-C present comparative plots demonstrating the OAK/antibiotic synergy against E. coli AG100, wherein FIG. 2A presents data of the accumulation of EtBr in bacteria suspended in PBS in presence of the specified exemplary OAK concentrations, FIG. 2B presents data showing the viability upon exposure to the exemplary OAK alone, or combinations of the OAK and erythromycin (dashed line represents the limit of detection), and FIG. 2C presents data of EtBr accumulation upon exposure to erythromycin in the presence of sub-MIC levels of the exemplary OAK (marked in solid lines) and the corresponding time-kill curves (marked in dashed lines);

FIGS. 4A-D present various means of characterization of OAK-mediated cochleates, wherein FIG. 4A presents the relative fluorescence intensities observed when exciting at 356 nm for MLVs of POPE:TOCL 75:25 (2.5 mg/ml) in the absence (solid line) and presence (dashed line) of an exemplary OAK (at a lipid to OAK ratio of 16) in PIPES pH 7.4 (20 mM PIPES, 0.14 M NaCl, 1 mM EDTA) at 37° C., whereas F is the observed fluorescence at any wavelength and Fmax is the fluorescence of the maximum value observed at 440 nm, set to 1 to normalize the curves; FIG. 4B presents the generalized polarization, as described by the equation $GP=I_{440}-I_{490}/I_{440}+I_{490}$ where $I_{440}$ and $I_{490}$ are the intensities at 440 nm and 490 nm respectively, when exciting at 356 nm or at 386 nm, whereas the lower bars were obtained with MLVs of POPE:TOCL (2.5 mg/ml) and taller bars correspond to MLVS in the presence of OAK at the conditions described in panel A; FIG. 4C presents the OAK encapsulation efficiency in liposomes (PC:PEG2000) and cochleates (POPE:TOCL) as determined by MIC and fluorescamine methods (white and gray, respectively), whereas the symbol "^" indicates >80%; and FIG. 4D presents the time-kill curves of *Klebsiella pneumoniae* cultured in whole blood in presence of 4 and 40 multiples of the MIC value ("▲" black triangle and "∇" inverted white triangle, respectively) of cochleate-encapsulated or liposome-encapsulated OAK (empty symbols and solid lines versus filled symbols and dotted line, respectively), "*" asterisk marks the plot of normal bacterial growth, "□" rectangle marks the plot of free (non-encapsulated) OAK at 4 multiples of the MIC value;

FIGS. 5A-B present comparative plots of the results of systemic efficacy studies in neutropenic mice, wherein FIG. 5A presents the survival experiment showing the individual contribution of erythromycin (5 mg/kg) or $C_{12}K-7\alpha_8$ (SEQ ID NO: 3) (5 mg/kg), whereas the mice (n=8/group) were inoculated IP with $3\times10^7$ CFU of *E. coli* (clinical isolate 14182) and treated 1 hour after infection by single IV administration of $C_{12}K-7\alpha_8$ (SEQ ID NO: 3) (free or cochleated) or free erythromycin; and FIG. 5B presents the survival rates of the infected mice (n=8/group) when treated by single IV administration of cochleates encapsulating both OAK and erythromycin;

FIGS. 6A-C present a series of light microscopy photographs of samples having the exemplary OAK polymer $C_{12}K-7\alpha_8$ (SEQ ID NO: 3) with lipid mixture DMPE:TOCL 75:25 (FIG. 6A), DPPE:TOCL 75:25 (FIG. 6B) and DMPE:DOPG 75:25 (FIG. 6C), showing the formation of large cochleates;

FIGS. 7A-I present a series of light microscopy photographs of samples having a lipid composition of POPE:TOCL 75:25 and the exemplary OAK polymers $C_{12}K-5\alpha_8$ (SEQ ID NO: 1) in FIG. 7A, $C_{12}K-6\alpha_8$ (SEQ ID NO: 2) in FIG. 7B, $C_{12}K-7\alpha_8$ (SEQ ID NO: 3) in FIG. 7C, $C_{12}K-8\alpha_8$ (SEQ ID NO: 4) in FIG. 7D, $C_{12}K-9\alpha_8$ (SEQ ID NO: 5) in FIG. 7E, $C_{12}K-11\alpha_8$ (SEQ ID NO: 6) in FIG. 7F, $C_{12}K-7\alpha_4$ (SEQ ID NO: 7) in FIG. 7G, $\alpha_{12}-7a8$ (SEQ ID NO: 8) in FIGS. 7H and $C_{12}K-7\alpha_{12}$ (SEQ ID NO: 9) in FIG. 7I;

FIGS. 8A-D present a series of light microscopy photographs of samples having anionic lipid compositions devoid of zwitterionic lipids, showing crystal-like structures in POPG:TOCL 75:25 with $C_{12}K-7\alpha_8$ (SEQ ID NO: 3) in FIG. 8A or DMPG:TOCL 75:25 with $C_{12}K-5\alpha_8$ (SEQ ID NO: 1) in FIG. 8B, and mostly liposomes in DMPG:TOCL 75:25 with $C_{12}K-7\alpha_8$ (SEQ ID NO: 3) in FIG. 8C or with $C_{12}K-9\alpha_8$ (SEQ ID NO: 5) in FIG. 8D;

DESCRIPTION OF EMBODIMENTS OF THE INVENTION

Figure 1:
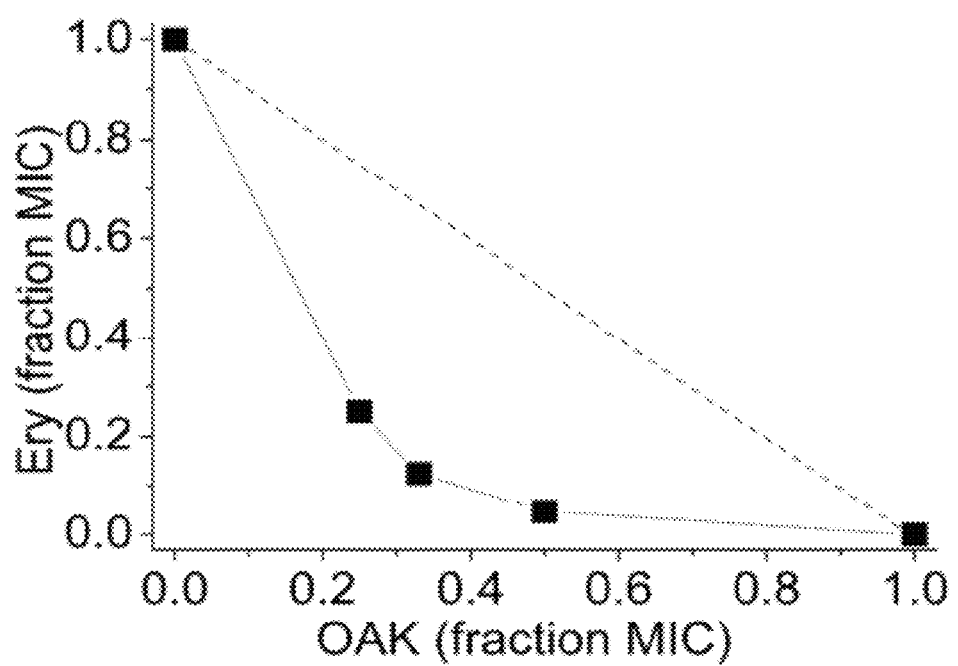
FIG. 1 presents comparative plots of MIC fraction of an exemplary antibiotic erythromycin versus the MIC fraction of an exemplary OAK $C_{12}K$-$7\alpha_8$ (SEQ ID NO: 3), showing synergistic inhibitory activity of the OAK and the antibiotic agent upon E. coli CI-14182, wherein the solid line represents changes in MIC of individual compounds when both drugs are present in combination, and the dashed line represents the hypothetical additive effect and the squares represent the MIC evolution for each drug.

The present invention, in some embodiments thereof, relates to pharmaceuticals and more particularly, but not exclusively, to novel cochleate-based systems and uses thereof as drug delivery vehicles in the treatment of medical conditions such as, for example, conditions associated with antibiotic-resistant pathogenic microorganisms.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, polymers composed of positively charged amino acid residues and ω-amino fatty acid moieties, also referred to herein and in the art as OAK polymers, were found to exhibit an antimicrobial activity, while overcoming the limitations associated with administration of antimicrobial peptides. These polymers were also found to exhibit a re-sensitization effect, when used in combination with an antibiotic agent, so as to re-sensitize a pathogenic microorganism that has already developed resistance to the antibiotic agent.

Without being bound by any particular theory, it has been proposed that OAK polymers exert antimicrobial activity by breaching the cytoplasmic membrane permeability barrier of microorganisms. While studying the mechanism of action of OAK polymers, the present inventors have attempted to form a complex between an antimicrobial OAK polymer and a lipid bilayer that mimics the cytoplasmic membrane of some microorganisms, and thereby surprisingly uncovered that such a complex affords cochleate structures, namely turbinated multilamellar lipid bilayer cigar-like structures.

The formation of cochleates from the studied molecular systems was particularly unexpected since heretofore, it has been thought that cochleates are formed only from specific phospholipids mixtures, and only in the presence of multivalent metal cations such as $Ca^{2+}$—none of which were part of the molecular systems used in the studies conducted by the present inventors.

Thus, the present inventors have uncovered that novel cochleate systems can be obtained in the presence of OAK polymers.

Polymer-Mediated Cochleate Systems:

The novel cochleate systems disclosed herein are also referred to herein interchangeably as "compositions-of-matter".

Hence, according to an aspect of embodiments of the present invention, there is provided a composition-of-matter which comprises a cochleate and a polymer encapsulated therein, wherein the cochleate is being formed from a mixture of at least two phospholipids, and the polymer comprises a plurality of positively charged amino acid residues and at least one ω-amino-fatty acid moiety, wherein the ω-amino-fatty acid moiety is covalently linked to at least two positively charged amino acid residues via the N-alpha of one amino acid residue and via the C-alpha of the other amino acid residue.

The Polymer:

Thus, a polymer as utilized in any of the embodiments described herein is composed of a plurality of positively charged amino acid residues and one or more ω-amino-fatty acid moieties, as these terms are defined herein, wherein the ω-amino-fatty acid moiety is being covalently linked to at least two amino acid residues in the sequence of the polymer via the N-alpha of one amino acid residue and via the C-alpha of the other amino acid residue in the sequence.

Each of the polymers, according to embodiments of the invention, comprises a polymeric backbone composed of three or more units, also referred to herein interchangeably as residues or moieties, and accordingly comprises a chain made of a sequence of positively charged amino acid residues, interrupted by one or more ω-amino-fatty acid moieties and terminated by modified or unmodified amino acid residues, as is further detailed hereinafter.

As used herein throughout the term "amino acid" or "amino acids" is understood to include the 20 genetically coded amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids and other non-naturally occurring amino acids.

As used herein, the phrase "unit" describes a sub-part, such as a monomer, of a molecular entity, such as a polymer. The unit is typically a residue of a molecule which underwent a chemical reaction and is now covalently linked to other units in the molecular entity. The term "unit" is used herein in the context of the molecular entity, e.g. the polymer according to some embodiments of the present invention.

As used herein, the phrase "moiety" describes a part, and preferably a major part, of a chemical entity or compound, which typically has certain functionality or distinguishing features. According to some embodiments of the present invention, the term "moiety" corresponds to the term "unit" but in the context of the parent molecule which turned into a unit of the molecular entity (e.g., the polymer).

As is well accepted in the art in the molecular context, the term "residue", as used herein, refers to a portion, and typically a major portion of a molecular entity, such as molecule or a part of a molecule such as a group, which has underwent a chemical reaction and is now covalently linked to another molecular entity. In the context of the present embodiments, a residue is an equivalent term to a monomeric unit within the polymer, thus the aforementioned "unit" and/or "moiety".

For example, the parent molecule can be an amino acid molecule, and the portion of the amino acid which forms a part of a polypeptide chain (or a polymer as described herein) after the formation of the polypeptide chain, is a unit in the form of an amino acid residue (a unit or a monomer). An amino acid residue is therefore that part of an amino acid which is present in a peptide sequence upon reaction of, for example, an alpha-amine group thereof with an alpha-carboxylic group of an adjacent amino acid in the peptide sequence, to form a peptide amide bond and/or of an alpha-carboxylic acid group thereof with an alpha-amine group of an adjacent amino acid in the peptide sequence, to form a peptide amide bond. Similarly, the term "residue" refers to a unit in the form of an ω-amino-fatty acid moiety.

As used herein, the phrase "hydrophobic moiety" describes a chemical moiety that has a minor or no affinity to water, that is, which has a low or no dissolvability in water and often in other polar solvents. Exemplary suitable hydrophobic moieties for use in the context of the present embodiments, include, without limitation, hydrophobic moieties that consist predominantly of one or more saturated or unsaturated, branched or unbranched hydrocarbon chains and/or aromatic rings, and optionally one or more functional groups which may be non-hydrophobic, but do not nullify the overall hydrophobicity of the hydrophobic moiety. Representative examples of hydrophobic moieties include, without limitation, fatty acids, ω-amino-fatty acids, hydrophobic amino acids (amino acids with hydrophobic side-chains), alkanes, alkenes, aryls and the likes, as these terms are defined herein, and any combination thereof.

The term "side-chain", as used herein with reference to amino acids, refers to a chemical group which is attached to the α-carbon atom of an amino acid. The side-chain is unique for each type of amino acid and typically does not take part in forming the peptide bond in a naturally occurring protein or polypeptide, but can be used to form a link between monomers in the polymer presented herein in cases the side-chain comprises a suitable functional group. For example, the side chain for glycine is hydrogen, for alanine it is methyl, for valine it is isopropyl, for phenylalanine it is benzyl, and the side chain for lysine can be regarded as an amino-butyl group, e.g., having an available amine group. For the specific side chains of all amino acids reference is made to A. L. Lehninger's text on Biochemistry (see, chapter 4).

According to some embodiments of the present invention, the units of the polymer are covalently linked to one another via peptide bonds.

The terms "peptide bond" and "amide bond" as used herein refer to an amide group, namely, a —(C=O)NH— group, which is typically formed by nucleophilic addition-elimination reaction between a carboxylic group and an amine group, as these terms are defined herein.

However, the polymers described herein may have other bonds linking the various components in the polymeric structure. Such non-peptidic bonds may render the polymer more stable while in a body or more capable of penetrating into cells. Thus, peptide bonds (—(C=O)NH—) within the polymer may be replaced, for example, by N-methylated amide bonds (—(C=O)NCH$_3$—), ester bonds (—C(R)H—C(=O)—O—C(R)—N—), ketomethylen bonds (—C(=O)CH$_2$—), aza bonds (—NH—N(R)—C(=O)—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—(C=O)—), peptide derivatives (—N(R)—CH$_2$—C(=O)—), wherein R is the "normal" side chain, naturally presented on the carbon atom. These modifications can occur at any of the bonds along the polymer chain and even several (2-3) at the same time.

In some embodiments, all of the bonds in the polymer, linking the various units to each other, are peptide bonds. For example, in one embodiment, the polymer is made of an amino acid residue linked by a peptide bond to an ω-amino fatty acid moiety which in turn is linked to a second amino acid residue by another peptide bond. In another example, the polymer of the previous example is elongated by a second ω-amino fatty acid moiety or a fatty acid moiety which is linked to any one of the N- or C-termini by a peptide bond, and so forth.

The net positive charge of the polymer at physiological conditions, which is one of the characteristics of the polymers according to some embodiments of the present invention, and which was found to be linked to their activity, is maintained by having one or more positively charged amino acid residues in the polymer, optionally in addition to the positively charged N-terminus amine present in "classical" peptides.

As used herein the phrase "positively charged amino acid" describes a hydrophilic amino acid with a side chain pKa value of greater than 7, namely a basic amino acid. Basic amino acids typically have positively charged side chains at physiological pH due to association with a hydronium ion. Naturally occurring (genetically encoded) basic amino acids include lysine (Lys, K), arginine (Arg, R) and histidine (His, H), while non-natural (non-genetically encoded, or non-standard) basic amino acids include, for example, ornithine, 2,3,-diaminopropionic acid, 2,4-diaminobutyric acid, 2,5,6-triaminohexanoic acid, 2-amino-4-guanidinobutanoic acid, and homoarginine.

In some embodiments, all the amino acid residues in the polymer are positively charged amino acid residues. Exemplary polymers according to some embodiment comprise a plurality of lysine residues. However, other positively charged amino acids as described herein are also contemplated.

The term "ω-amino-fatty acid" refers to fatty acids which feature an amino group at the distal carbon of the hydrocarbon chain thereof.

The ω-amino-fatty acid moieties that are used in the context of embodiments of the present invention have one or more saturated or unsaturated hydrocarbon chains, and are capable of linking to one or two other units in the polymer (e.g., one or two of an amino acid residue and another ω-amino-fatty acid moiety) via two peptide bonds. These moieties therefore preferably have a carboxylic group at one end of the hydrocarbon chain (for linking a free amine group) and an amine group at the other (for linking a carboxylic acid group). The hydrocarbon chain connecting the carboxylic and amine groups in such an ω-amino-fatty acid moiety typically has from 3 to 30 carbon atoms.

Exemplary ω-amino-fatty acids include, without limitation, 4-amino-butyric acid, 6-amino-caproic acid, 8-aminocaprylic acid, 10-amino-capric acid (10-amino-decanoic acid), 12-amino-lauric acid (12-amino-dodecanoic acid), 14-amino-myristic acid (14-amino-tetradecanoic acid), 14-amino-myristoleic acid, 16-amino-palmitic acid (16-amino-hexadecanoic acid), 18-amino-stearic acid, 18-amino-oleic acid, 16-amino-palmitoleic acid, 18-amino-linoleic acid, 18-amino-linolenic acid and 20-amino-arachidonic acid.

The polymer as described herein, may have more then one ω-amino-fatty acid moieties as defined hereinabove, whereby one or more ω-amino-fatty acid moieties are each linked to one amino acid at one end and to another amino acid residue at another end, and another ω-amino-fatty acid moiety may elongate the polymeric chain by being linked to either one of the termini thereof, for example to the N-alpha of a terminal amino acid residue and/or the C-alpha of a terminal amino acid residue. Optionally, another ω-amino-fatty acid moiety may be linked to a side-chain of an amino acid residue in the polymer.

The polymer, according to some embodiments of the present invention, includes from 2 to 50, or from 2 to 30, or from 2 to 20 positively charged amino acid residues. Optionally, the polymer includes from 2 to 12 positively charged amino acid residues.

The polymer, according to some embodiments, includes from 1 to 50, or from 1 to 30, or from 1 to 20 ω-amino-fatty acid moieties. Optionally, the polymer includes from 1 to 12 ω-amino-fatty acid moieties.

The polymers described herein can be represented collectively by the following general Formula I:

X-W$_0$-[A$_1$-Z$_1$-D$_1$]-W$_1$-[A$_2$-Z$_2$-D$_2$]-W$_2$- . . . [An-Zn-Dn]-Wn-Y      Formula I wherein:

n is an integer from 2 to 50, or from 2 to 12.

A$_1$, A$_2$, . . . , An are each independently a positively charge amino acid residue as described herein, such as lysine residues, histidine residues, ornithine residues and arginine residues. In some embodiments all of the positively charged amino acid residues A$_1$, A$_2$, . . . , An are lysine residues.

D$_1$, D$_2$, . . . , Dn are each independently a ω-amino-fatty acid moiety, as described herein, or absent, provided that at least one such ω-amino-fatty acid moiety exists in the polymer.

Linking moieties connecting each monomer of the polymer, denoted Z$_1$, Z$_2$, . . . , Zn and W$_0$, W$_1$, W$_2$, . . . , Wn, each of which independently linking an amino acid residue and a ω-amino-fatty acid moiety or absent. In some embodiments at least two of the linking moieties are peptide bonds and in other embodiments all the linking moieties are peptide bonds.

The fringes of the polymer, denoted X and Y, may each independently be hydrogen, an amine, an amide, an amino acid residue, a hydrophobic moiety, an ω-amino-fatty acid moiety, a fatty acid moiety or absent.

In some embodiments of the present invention, a fatty acid moiety exhibits a hydrocarbon chain that can be unbranched and saturated, branched and saturated, unbranched and unsaturated or branched and unsaturated, namely each can have one or more unsaturated parts (double bonds) and one or more substituents along their hydrocarbon chain. Non-limiting example of such fatty acid residues are butyric acid residue (4 carbons), γ-aminobutyric acid residue and α-aminobutyric acid residue, hexanoic acid residue (6 carbons), caprylic acid residue (8 carbons), decanoic acid residue (10 carbons), 5-dodecenoic acid residue, dodec-7-enoic acid residue, lauric acid residue (12 carbons), tetradecanoic acid residue (14 carbons), myristoleic acid residue, tetradec-5-enoic acid residue, tetradec-9-enoic acid residue, palmitic acid residue (16 carbons), hexadec-7-enoic acid residue, hexadec-9-enoic acid residue, palmitoleic acid ((Z)-9-hexadecenoic acid, which is a monounsaturated fatty acid) residue and oleic acid ((Z)-9-octadecanoic acid, which is a monounsaturated fatty acid) residue.

Unless stated otherwise, the use of the terms "polymer" and "polymers" herein refers to both the linear cyclic and/or the cyclic linear form thereof.

The term "linear" as used herein in the context of the polymers, refers to a non-cyclic polymer, i.e., a polymer which have two termini and its backbone or amino-acid side-chains do not form a closed ring.

The term "cyclic" as used herein in the context of the polymer, refers to a polymer that comprises an intramolecular covalent bond between two non-adjacent residues (monomers) therein, forming a cyclic polymer ring.

Cyclic polymers comprising a plurality of positively charged amino acid residues and at least one ω-amino-fatty acid moiety attached thereto are described in details in U.S. Patent Application No. 20100120671, WO 2008/132738 and WO 2009/090648, all by one of the present inventors, and all being incorporated by reference as if fully set forth herein.

Exemplary linear OAK polymers, according to some embodiments of the present invention, are linear OAK polymers such as those having the structures presented hereinbelow:

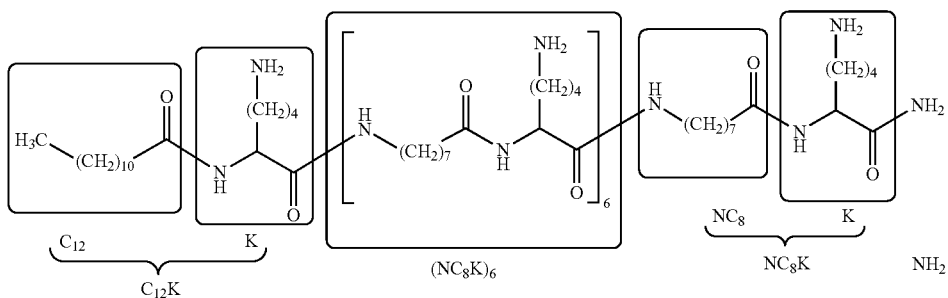
which is also referred to herein as $C_{12}K(NC_8K)_7NH_2$ (SEQ ID NO: 3), or as $C_{12}K\text{-}7\alpha_8$;
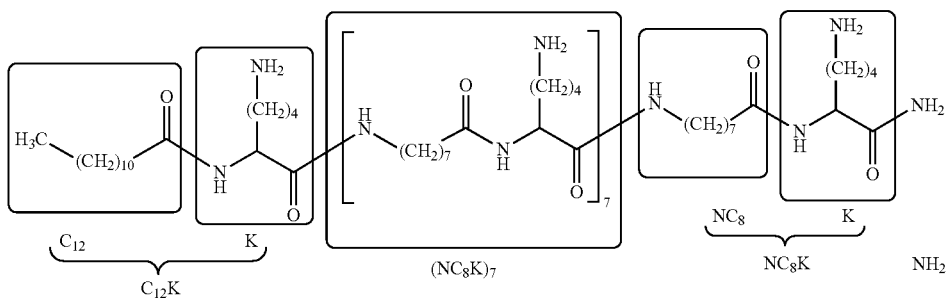
which is also referred to herein as $C_{12}K(NC_8K)_8NH_2$ (SEQ ID NO: 4), or as $C_{12}K\text{-}8\alpha_8$;
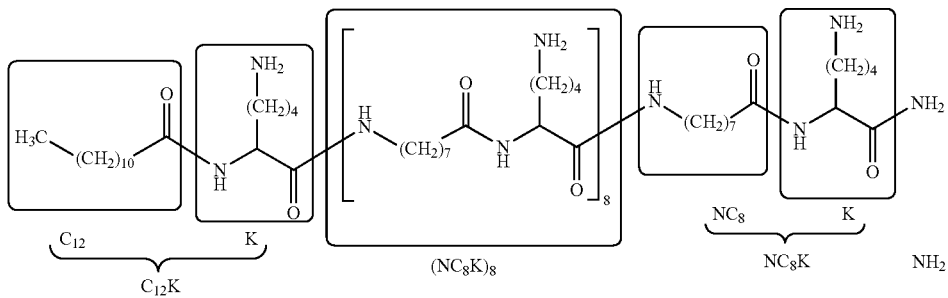
which is also referred to herein as $C_{12}K(NC_8K)_9NH_2$ (SEQ ID NO: 5), or as $C_{12}K\text{-}9\alpha_8$;
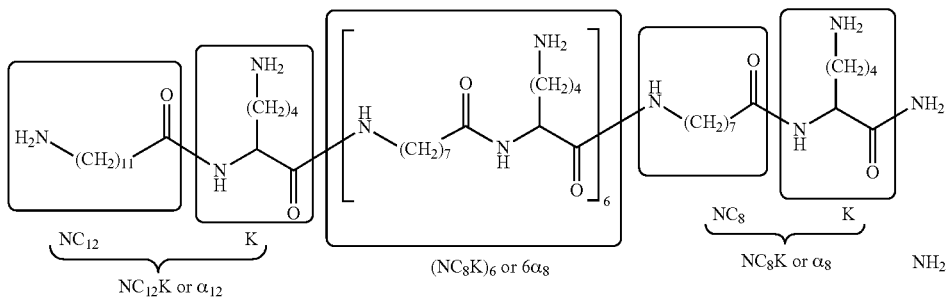

which is also referred to herein as NC$_{12}$K(NC$_8$K)$_7$NH$_2$ (SEQ ID NO: 8), or as α$_{12}$-7α$_8$; and

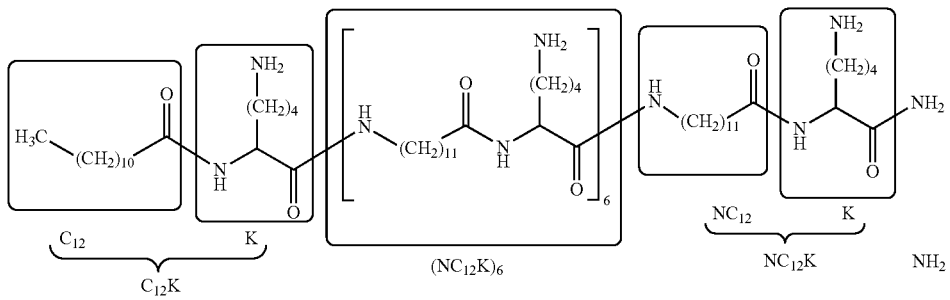

which is also referred to herein as C$_{12}$K(NC$_{12}$K)$_7$NH$_2$ (SEQ ID NO: 9), or as C$_{12}$K-7α$_{12}$.

As can be seen from the alternative denotation of the polymers, the sequence of an OAK polymer can be presented using abbreviations to note repeats of combinations of polymer units. Hence, a consecutive repeat of combined units of a ω-amino-fatty acid moiety attached to a lysine residue is denoted "mα$_n$," wherein "α" denotes an ω-amino-fatty acid moiety, "n" is the number of carbon atoms in the ω-amino-fatty acid moiety, and "m" is the number of consecutive repeats of the combined units.

According to some embodiments, the polymer comprises from 2 to 12, or from 4 to 12 NC$_{4-12}$K combined units, or from 6 to 10 NC$_{4-12}$K combined units.

According to some embodiments, the polymer comprises from 2 to 12, or from 4 to 12 NC$_8$K combined units, or from 6 to 10 NC$_8$K combined units.

According to some embodiments, the polymer comprises from 2 to 12, or from 4 to 12 consecutive NC$_{4-12}$K combined units (4-12α$_{4-12}$), or from 6 to 10 consecutive NC$_{4-12}$K combined units (6-10α$_{4-12}$).

According to some embodiments, the polymer comprises from 2 to 12 or from 4 to 12 consecutive NC$_8$K combined units (4-12α$_8$), or from 6 to 10 consecutive NC$_8$K combined units (6-10α$_8$).

Other exemplary polymers according to some embodiments of the present invention, are also presented in U.S. Pat. No. 7,504,381, WO 2006/035431, WO 2008/132738 and WO 2009/090648, and U.S. Patent Application Nos. 20070032428 and 20100120671, all being incorporated by reference as if fully set forth herein.

According to some embodiments of the present invention, polymers which exhibit a capacity to promote the formation of cochleates are characterized by a net positive charge that ranges from 6 to 12 or from 8 to 10. This net positive charge stems from the positive groups of the positively charged amino acid residues and the optional positively charged N-terminus of the polymer; hence a polymer which exhibits a larger number of positively charged amino acid residues will tend to have a larger net positive charge.

Another source of a positive charge is the N-terminus of the polymer, which can be the amino group of an amino acid residue, or the amino group of an ω-amino-fatty acid moiety attached to the amino acid residue at the N-terminus of the polymer.

As demonstrated in the Examples section that follows, polymers which exhibit a capacity to form cochleates also have a fatty acid moiety or an ω-amino-fatty acid moiety exhibiting a relatively long hydrocarbon chain. Hence, according to some embodiments of the present invention, the N-terminus of the polymer is a lysine residue having a NC$_{10-16}$ fatty acid moiety (e.g., a NC$_{12}$ fatty acid moiety or a 12-amino-fatty acid moiety) attached thereto, or a lysine residue having a C$_{10-16}$ fatty acid moiety (e.g., a C$_{12}$ fatty acid moiety) attached thereto.

According to some embodiments of the present invention, the C-terminus of the polymer is capped by an amide group, thereby neutralizing its negative charge.

According to some embodiments of the invention, the ω-amino-fatty acid moieties within the polymeric backbone exhibit a hydrocarbon chain of 6-10 carbon atoms. Exemplary such amino acid moieties include, but are not limited to, 4-amino-butyric acid moiety, 6-amino-caproic acid moiety, 8-amino-caprylic acid moiety, 10-amino-capric acid moiety and 12-amino-lauric acid moiety.

As demonstrated in the Examples section that follows, polymers which exhibit a notable capacity to form cochleates include ω-amino-fatty acid moieties of 8-carbon atoms, namely an 8-amino-caprylic acid moiety.

The present embodiments further encompass any enantiomers, diastereomers, prodrugs, solvates, hydrates and/or pharmaceutically acceptable salts of the polymers or of the compositions-of-matter described herein.

As used herein, the term "enantiomer" refers to a stereoisomer of a polymer that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active polymer (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the polymer as described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent polymer and its counter ion, which is typically used to modify the solubility characteristics of the parent compound and/or to reduce any significant irritation to an organism by the parent polymer, while not abrogating the biological activity and properties of the administered polymer. An example, without limitation, of a pharmaceutically acceptable salt would be a carboxylate anion and a cation such as, but not limited to, ammonium, sodium, potassium and the like.

The Phospholipid Mixture:

Typical lipid bilayers which are suitable for forming liposomes, vesicles or cochleates are formed from a mixture of two or more phospholipids. The head-group charge and size, and the length, saturation and number of the acyl-functionalities determine the characteristics of the lipid bilayers, since these govern the interactions between the lipids, and consequently the nature of the structure which is afforded from any given phospholipid mixture. The interactions between the phospholipids in the mixture determine its melting temperature, as defined hereinbelow, the curvature of the bilayer and the capacity of certain factors to incorporate into the bilayer and promote the formation of cochleates, according to some embodiments of the present invention.

The choice of a particular phospholipid mixture will also allow optimizing the biological and pharmacological characteristics of the resulting cochleates. One exemplary feature to consider is the intrinsic bilayer curvature, since the morphology of the lipids changes from a flat structure to a curved structure when cochleates are formed.

As exemplified hereinbelow, the composition of this mixture also determines the degree of the tendency to form cochleates in the presence of a polymer according to some embodiments of the present invention.

At a given temperature a lipid bilayer can exist in either a liquid or a gel (solid) phase. All lipids and mixtures thereof exhibit a characteristic temperature at which they undergo a transition from the gel to liquid phase (melt), and this temperature is referred to herein as the "melting temperature" or by the abbreviation "Tm".

While reducing the present invention to practice, the present inventors have found that the melting temperature of the phospholipid mixture can be used to predict if the molecular system of the mixture and the polymer would form cochleate structures on the presence of the polymers described herein.

Hence, the phospholipid mixture from which a cochleate is formed, according to some embodiments of the present invention, is characterized by a melting temperature higher than 10° C., or alternatively a melting temperature higher than 30° C., higher than 40° C., or higher than 50° C.

In some embodiments, the phospholipid mixture is characterized by a melting temperature that ranges from 10-55° C., or from 15-45° C. It has been found that mixtures with a melting temperature higher than 55° C. do not tend to form closed cochleate structures, presumably due to the instability of such structures that require higher temperature during preparation.

In some embodiments, the phospholipids used for forming the mixture are selected based on the known melting temperatures of each phospholipid, so that the resulting mixture has a predicted melting temperature in the desired range, as indicated hereinabove (e.g., from 15 to 45° C.).

The melting temperature of any given phospholipid mixture is also determined by the functional groups of each of the phospholipids, which participate in the inter-molecular interactions and hydrogen-bond network which contribute to the super-molecular stability of the lipid bilayer and any multi-lamellar structure which stems therefrom, such as a cochleate structure. The functional groups of the phospholipids also determine the extent to which the lipid surface is hydrated. Phospholipids with headgroups that form strong interlipid hydrogen bonds have less interaction with water and tend to be better in forming cochleates.

In some embodiments of the invention, the phospholipids mixture used in the formation of cochleates features a negative charge, presumably in order to be cross-linked by the positively charged polymer. Hence, exemplary phospholipids that are suitable for use in the phospholipid mixture according to some embodiments of the present invention include, but are not limited to, a zwitterionic phosphatidylcholine, a zwitterionic phosphatidylethanolamine, an anionic phosphatidylglycerol and an anionic diphosphatidylglycerol.

For example, 1-2-dimyristoyl-phosphatidylcholine (DMPC) is an exemplary zwitterionic phosphatidylcholine; 1-2-dimyristoyl-phosphatidylethanolamine (DMPE) is an exemplary zwitterionic phosphatidylethanolamine; 1-2-dimyristoyl-phosphatidylglycerol (DMPG) is an exemplary anionic (negatively charged) phosphatidylglycerol; 1-2-dioleoyl-phosphatidylethanolamine (DOPE) is an exemplary zwitterionic phosphatidylethanolamine; 1-2-dioleoyl-phosphatidylglycerol (DOPG) is an exemplary anionic (negatively charged) phosphatidylglycerol; 1-2-dipalmitoyl-phosphatidylethanolamine (DPPE) an exemplary anionic zwitterionic phosphatidylethanolamine; 1-palmitoy-2-oleoyl-phosphatidylcholine (POPC) is an exemplary zwitterionic phosphatidylcholine; 1-palmitoyl-2-oleoyl-phosphatidylethanolamine (POPE) is an exemplary zwitterionic phosphatidylethanolamine; tetramyristoyl-cardiolipin (TMCL) is an exemplary anionic diphosphatidylglycerol; and tetraoleoyl-cardiolipin (TOCL) is an exemplary anionic diphosphatidylglycerol.

According to some embodiments of the present invention, at least one of the phospholipids in the mixture is a zwitterionic phosphatidylethanolamine.

According to some embodiments of the present invention, at least one another phospholipid in the mixture is an anionic diphosphatidylglycerol.

According to some embodiments of the present invention, at least one of the phospholipids in the mixture is selected from the group consisting of POPG, POPE, POPC, DPPE, DOPE, DMPG, DMPE and DMPC, and another phospholipid is selected from the group consisting of TOCL and DOPG. These and other abbreviations to the chemical names of exemplary phospholipids are interpreted hereinabove and also under "Materials and Experimental Methods" in the Examples section that follows below.

A binary phospholipid mixture (comprising two phospholipids) is also characterized by the relative molar ratio of the phospholipids, and can be denoted by two numbers representing the mol percentage of each phospholipid. For example, a mixture comprising two phospholipids at equal mol percentage will be denoted by the molar ratio of 50:50. Alternatively, the molar ratio can be denoted by the relative part of each phospholipid, namely a 1:1 molar ratio would denote the aforementioned exemplary mixture. A tertiary phospholipid mixture would be denoted by three numbers (percentages or parts), a quaternary mixture is denoted by four numbers and so forth.

As presented in the Examples section that follows, exemplary phospholipid mixtures include, without limitation a DMPE:TOCL mixture, a DPPE:TOCL mixture, and a DMPE:DOPG mixture.

According to some embodiments of the present invention, a respective molar ratio of the aforementioned phospholipids in a mixture ranges from 1:1 to 9:1, or alternatively, the molar ratio is 3:1.

According to some embodiments of the present invention, an exemplary mixture comprises DMPE and TOCL at a molar ratio of 3:1; DPPE and TOCL at a molar ratio of 3:1 or DMPE and DOPG at a molar ratio of 3:1.

As indicated hereinabove, other phospholipid characteristics play a role in driving the system to form cochleates. In this regard the DMPC:TOCL mixture has a lesser tendency to form negative curvatures since the PC headgroup is larger than the PE headgroup; the mixture of DMPE:TOCL has a greater tendency to form negative curvatures, which lead to cochleate formation; the mixture of DOPE:TOCL has a greater tendency to form negative curvatures due to the higher acyl chain unsaturation, than that of the DMPE:TOCL mixture; and so forth. Nonetheless, curvature tendency is not necessarily a predictor of cochleate formation.

It is noted herein that one of the unexpected results of the cochleate formation experiments is that the cochleates which are formed in the presence of a polymer according to some embodiments of the present invention, were formed from phospholipid mixtures which are essentially devoid of phosphatidylserine and/or multivalent (e.g., divalent) metal cations. It is also noted that cochleates reported hitherto where afforded when phosphatidylserine and $Ca^{+2}$ were present.

The Process:

Preparation of the polymer-mediated cochleates according to some embodiments of the present invention, opens with the selection of suitable phospholipids which will form a phospholipid mixture having the appropriate characteristics, such as charge, melting temperature, curvature tendency, biological compatibility (degradability, metabolism, toxicity, target-mimicking and the likes) and other attributes which suite the intended use of the composition-of-matter. The selected phospholipids are typically dissolved in a solution of organic solvents and mixtures thereof, such as chloroform and methanol, and thereafter the solvent is evaporated to afford a dehydrated film. The dry phospholipid mixture film is then hydrated with an aqueous solution of a polymer in a buffer to produce a suspension of the phospholipid mixture and the polymer, typically in a molar ratio which ranges from 5:1 to 15:1 lipids to polymer. Co-encapsulation of a polymer with any given bioactive agent in cochleates is afforded by a similar process, using a co-solution of the polymer and the bioactive agent for the re-hydration step.

It is noted herein that during the process of preparing polymer-mediated cochleates according to some embodiments of the present invention, there is essentially no use of phosphatidylserine nor is there any use of a multivalent metal cation. Hence, according to some embodiments of the present invention, the phospholipid mixture used in the process presented herein is essentially devoid of phosphatidylserine, and further the process is performed in the absence of a multivalent metal cation such as $Ca^{2+}$.

A New Polymer:

In the course of the studies presented herein, a new polymer has been prepared and practiced. Thus, according to an aspect of some embodiments of the invention, there is provided the polymer:

which is also referred to herein as $C_{12}K(NC_8K)_{11}NH_2$ (SEQ ID NO: 6), or as $C_{12}K\text{-}11\alpha_8$.

As demonstrated in the Examples section that follows, this polymer exhibits antimicrobial activity, and can therefore be utilized as antimicrobial agent per-se or in various pharmaceutical compositions identified for use in the treatment of medical conditions associated with pathogenic microorganisms, as well as to form a part of a composition-of-matter according to some embodiments of the present invention.

Activity of the Polymer-Mediated Cochleate Systems:

As discussed herein and elsewhere, the polymer which forms a part of the cochleate according to some embodiments of the present invention, may exhibit biologic activity per se, as disclosed in, for example, U.S. Pat. No. 7,504,381, WO 2006/035431, and U.S. Patent Application Nos. 20070032428 and 20100120671.

As further disclosed for example, in WO 2009/090648, the polymer exhibits an antibiotic re-sensitization activity and can be utilized in combination with the antibiotic agent.

Accordingly, in some embodiments, a composition-of-matter as described herein is identified for use in the treatment of a medical condition which is treatable by a polymer as described herein.

Thus, for example, a composition-of-matter as described herein, which comprises a polymer that has an antimicrobial activity, can be used in the treatment of a medical condition associated with a pathogenic microorganism, as defined herein.

Such a composition-of-matter can be used in combination with an antibiotic agent, which either acts in synergy with or in addition to the polymer or to which the polymer sensitizes or re-sensitizes the pathogenic microorganism in case of a resistance to the antibiotic agent.

A composition-of-matter as described herein, which comprises a polymer that has an anticancerous activity, can be used in the treatment of cancer.

Such a composition-of-matter can be used in combination with an anticancerous agent, as previously described for anticancerous polymers. Such a composition-of-matter is useful in the treatment of MDR cancer, presumably by affecting the P-glycoprotein pumps that induce efflux of cytotoxic drug, as previously described in the context of the disclosed polymers.

The use of the compositions-of-matter described herein in treating medical conditions is effected by using the cochleate as a vehicle for delivering the polymer to a desired bodily site in a subject. The cochleate serves as a protecting medium for the encapsulated polymer and further serves as a medium that enables to control the release of the polymer.

In the context of embodiments of the present invention, a subject is a human or an animal inflicted with a medical condition that can be treated with a polymer as described herein, with a bioactive agent as described herein or by a combination thereof, as described herein.

Without being bound by any particular theory, it is assumed that the polymer is released from the cochleate into a physi-

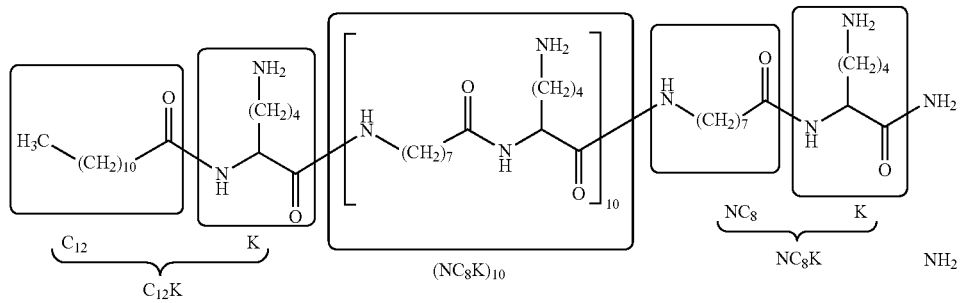

ological environment as a result of degradation of the cochleate in this environment. The degradation can be partial, such that allows diffusion of the polymer from the cochleate matrix into the physiological environment, or complete. It is thus further assumed that the release profile of the polymer is determined by its concentration in the cochleate, as diffusion rate is also governed thereby.

Stemming from the above, the polymer-mediated cochleate may also effect a controlled release of the encapsulated polymer, and if present, also of the co-encapsulated bioactive agent. The controlled release is afforded by the gradual and prolonged degradation of the multilamellar structure of the cochleate. The rate of degradation depends, at least in part, on the composition of the phospholipid mixture and the type and concentration of the polymer.

Hence, according to some embodiments of the present invention, the phospholipid mixture and the concentration of the polymer are selected such that a therapeutically effective amount of the biologically active polymer is released under physiological conditions.

The therapeutically effective amount of the biologically active polymer corresponds essentially to the amount of the released polymer that is present in the physiological environment. Being in the cochleate encapsulated form affects the rate of the release of the biologically active polymer into the environment, thereby affecting its pharmacokinetic profile in terms of absorption, distribution, metabolism, excretion and toxicity.

Accordingly, while the phospholipid mixture used to form the cochleate, and the type of polymer present during the cochleate formation determine the degradation rate of the cochleate (as demonstrated herein) and accordingly the release profile of the polymer, these parameters can be selected so as to determine the release profile of the polymer. Additionally, or alternatively, the polymer's concentration of the system is selected so as to determine the release profile of the polymer.

By selecting a phospholipid mixture, a polymer type and/or a polymer concentration, a desired release profile of the polymer for an indicated use can be determined.

Determination of the release profile of the polymer and/or a bioactive agent from the cochleate systems described herein can be performed using well-known assays for determining release profile. For example, medium-stability and drug release rates per any given cochleate formulation can be assessed using, for example, medium-resistant bacteria, wherein the bacteria, and a solution containing a non-encapsulated polymer or a polymer encapsulated in a cochleate are added to the medium, and bacterial survival is determined at various incubation time-points by measuring CFU counts. For example, for determining the optimal formulation of phospholipids and polymer that would afford the optimal release rate of drug from cochleates in human blood (so as to combat blood infections or other blood-borne pathogenic microorganisms), the assay can use human blood-resistant *Klebsiella pneumoniae* CI 1286 in whole human blood. Such procedure is demonstrated and the Examples section the follows and the results of such an assay are presented in FIG. 4, and discussed in details hereinbelow.

It is noted that encapsulating a biologically active polymer in the cochleate system described herein allows the administration of polymers at a concentration that is higher than the therapeutically effective amount thereof, and can be determined such that a release profile of the polymer is such that a therapeutically effective amount of the polymer is maintained at the desired bodily site, as described herein.

It is further noted that encapsulating a biologically active polymer in the cochleate system described herein allows the administration of polymers at a concentration that is otherwise (when not encapsulated) considered toxic to the subject, since the encapsulation thereof reduces its toxicity and controls the level of the released polymer in the physiological environment. The ability to administer higher amounts of the polymer to a subject ultimately increases the usability of the polymer as a drug, since the pathogens respond to the polymer in a dose-dependent manner, as demonstrated elsewhere and hereinbelow (for dose-dependent manner activity, see for example, FIG. 2).

Toxicity of encapsulated and non-encapsulated polymers can be determined by well-known assays. For example, maximal tolerated dose (MTD) can be determined in animal models using single dose intravenous (IV) injections of free and cochleate-encapsulated polymers.

For example, determining the MTD of encapsulated and free OAK is afforded by treating the mice by a single IV injection of either free or encapsulated combinations of OAK and/or an antibiotic agent. Following the treatments, the mice are inspected for adverse effects for several hours and mortality is monitored for several days thereafter. The obtained survival data are used to determine the effective increase in the concentration of the OAK afforded by encapsulation. Such in-vivo experimental procedure is demonstrated and the Examples section the follows and the results of such an assay are presented in FIG. 5, and discussed in details hereinbelow.

The experiments conducted have shown that the MTD of exemplary polymers has been reduced by 4-fold upon cochleate encapsulation. Additional experiments have shown higher reduction of the MTD upon encapsulation (data no shown).

Hence, the maximal tolerated dose (MTD) of an encapsulated polymer in the form of the composition-of-matter, according to some embodiments of the present invention, is higher by at least 2-fold, 3-fold, 4-fold, 8-fold, 12-fold, 20-fold and even higher, as compared to a maximal tolerated dose of the same polymer in an un-encapsulated form thereof.

It is noted that the reduced toxicity of the polymer when encapsulated in the cochleate allows using polymers which are otherwise toxic. Such a reduced toxicity further allows using a polymer concentration which is higher than its therapeutically effective amount (or its sensitizing or re-sensitizing effective amount). In some embodiments, such a higher concentration is desired for forming a cochleate, yet has been considered as above the MTD of a given polymer. The findings presented herein demonstrate the versatility and controllability of the pharmacokinetic properties of the polymer-mediated cochleate systems described herein.

In practice, the composition-of-matter according to some embodiments of the present invention can be identified for use in the treatment of a medical condition which is treatable by the biologically active polymer. Hence the composition-of-matter can be identified for use in the treatment of a medical condition associated with a pathogenic microorganism alone or in combination with other bioactive agents which are not necessarily co-encapsulated in the cochleate. Similarly, the composition-of-matter can be identified for use in the treatment of cancer alone or in combination with other bioactive agents which are not necessarily co-encapsulated in the cochleate. Furthermore, the composition-of-matter can be identified for use for sensitization or re-sensitization of microorganisms and cancerous cells to other bioactive agents which are not necessarily co-encapsulated in the cochleate.

Alternatively, the composition-of-matter according to some embodiments of the present invention further comprises a bioactive agent which is co-encapsulated in the cochleate. In such cases the cochleate can serve as a delivery vehicle for the bioactive agent to a desired bodily site.

The polymer-mediated cochleates according to some embodiments of the present invention can survive the harsh acid environment of the stomach of the subject; thereby provide protection of acid-susceptible bioactive agents encapsulated therein, probably by virtue of their unique multilayered turbinated structure.

Hence, according to some embodiments of the present invention, polymer-mediated cochleates can be used to co-encapsulate bioactive agents, such as peptides, glycopeptides, antigens and other molecules which otherwise would not sustain all physiological environments, such as the GI tract with its acid environment and digestive enzymes, and deliver them through these environments so as to allow them to reach a designated bodily side, once the cochleate eventually degrades, without compromising their activity.

Typically it is not expected that previously known cochleates would survive the stomach and protect an encapsulated bioactive agent from the acid environment and degradative enzymes, since it is known that without the presence of at least 3 mM calcium, previously known cochleates begin to unwind and form liposomes. Therefore previously known cochleates would be expected to degrade and come apart during the transit from the mouth, down the esophagus and through the stomach and be digested as food, leaving the unprotected bioactive agent to a similar fate. In sharp contrast, the presently disclosed cochleate systems, according to some embodiments of the present invention, do not relay on the presence of calcium.

A bodily site may be a biologic system such as the blood system, the nervous system and the lymph system, or an organ such as lungs, muscles, internal organs, brain or heart, or a type of tissue such as mucosal tissues, bone tissue and the likes, depending on the medical condition being treated and the role of the delivered bioactive agent.

Having survived the stomach, the polymer-mediated cochleates disclosed herein would interact in an effective way with the mucosal and circulating immune systems and deliver molecules which retain biologic activity at the delivery site within the host.

An antigen co-encapsulated and delivered by means of a polymer-mediated cochleate is expected to evoke an immune response, and possibly an intensified immune response. Hence, according to some embodiments of the present invention, the composition-of-matter can be used as an adjuvant in a pharmaceutical composition intended to evoke an immune response, such as a vaccine.

As used herein, the term "immune response" means either antibody, cellular, proliferative or cytotoxic activities, or secretion of cytokines.

The term "antigen", as used herein, is meant to indicate the polypeptide to which an immune response is directed or an expressible polynucleotide encoding that polypeptide.

Since, as discussed hereinabove, the concentration of the polymer is one of the factors that governs the chemical properties of the cochleate, it subsequently governs the rate of release and the therapeutic effective amount of the co-encapsulated bioactive agent, as described hereinabove. Hence, according to some embodiments of the present invention, the mixture and the concentration of the polymer are selected such that a therapeutic effective amount of the bioactive agent is released under physiological conditions.

When the co-encapsulated bioactive agent is an antibiotic agent, the composition-of-matter according to some embodiments of the present invention is identified for use in treating a medical condition associated with a pathogenic microorganism.

In some cases the polymer in the cochleate can exert sensitization or re-sensitization activity or act synergistically with respect to the co-encapsulated bioactive agent, such that the cochleate serves as a delivery vehicle for both the bioactive agent and the polymer.

The co-encapsulation of the polymer and the antibiotic agent affords a unique condition which allows using the composition-of-matter to combat resistant pathogenic microorganism successfully. Such activity is demonstrated in the Examples section that follows. Such a composition-of-matter is notably effective in cases where the resistance mechanism of the resistant pathogenic microorganism is substantially an efflux-enhanced drug resistance mechanism.

Antibiotic agents which are most prone to suffer a reduction in efficacy as a result of efflux-enhanced drug resistance mechanism are intracellular-targeting antibiotic agents. Exemplary intracellular-targeting antibiotic agents include, without limitation, erythromycin, clarithromycin, tetracycline, rifampicin and ciprofloxacin.

Exemplary resistant pathogenic microorganism include, without limitation, Gram-negative bacteria such as *E. coli* or Gram-positive bacteria such as *S. aureus*.

Additional examples of resistant Gram-negative bacteria include, but are not limited to, *Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella* spp., *Yersinia enterocolitica, Acinetobacter calcoaceticus, Flavobacterium* spp., *Haemophilus influenzae, Pseudomonas aeruginosa, Campylobacter jejuni, Vibrio parahaemolyticus, Brucella* spp., *Neisseria meningitidis, Neisseria gonorrhoea, Bacteroides fragilis,* and *Fusobacterium* spp.;

Additional examples of Gram positive bacteria include, but are not limited to, Strep.pyogenes (Group A), Strep.pneumoniae, Strep.GpB, Strep.viridans, Strep.GpD-(Enterococcus), Strep.GpC and GpG, Staph.epidermidis, *Bacillus subtilis, Bacillus anthraxis, Listeria monocytogenes,* Anaerobic cocci, *Clostridium* spp., and *Actinomyces* spp.

When the co-encapsulated bioactive agent is an antibiotic agent, the composition-of-matter according to some embodiments of the present invention may also be identified for use in re-sensitizing a pathogenic microorganism to the antibiotic agent. As stated herein, such re-sensitizing activity is disclosed in, for example, WO 2009/090648.

In some embodiments, the composition-of-matter according to some embodiments of the present invention may also be identified for use in sensitizing a resistant pathogenic microorganism to the antibiotic agent.

Polymers which exhibit antimicrobial re-sensitizing activity and are further characterized advantageously as effective re-sensitizing agents at concentrations well below there own bactericidal levels (below the concentration which eradicates the microorganisms), can be co-administered in the form of the composition-of-matter according to some embodiments of the present invention, when co-encapsulated with another antibiotic agent that became ineffective during a standard antimicrobial treatment in a subject, due to the emergence of resistance thereto.

As demonstrated in the Examples section that follows, compositions-of-matter comprising polymer-mediated cochleates with a co-encapsulated antibiotic were found highly effective in eradicating resistant bacteria. These compositions-of-matter were shown capable of re-sensitizing bacteria which became resistant to an antibiotic, such that when the same antibiotic is re-used, it effectively eradicates the bacteria. These compositions-of-matter further act by sensitizing an antibiotic-resistant bacteria in general.

The compositions-of-matter having a co-encapsulated antibiotic agent according to some embodiments of the present invention, are therefore highly useful in treating conditions associated with resistant bacteria, by (i) being effective when co-encapsulating an antibiotic agent that would otherwise not be effective; (ii) being effective in preventing an emergence of resistance to an antibiotic agent, when co-encapsulating the antibiotic agent; (iii) being effective is sensitizing a antibiotic agent to which the a pathogenic agent is resistant; and (iv) being effective in re-sensitizing a microorganism to the co-encapsulated antibiotic agent, upon an antimicrobial treatment that resulted in emergence of resistance to the antibiotic agent when used alone.

Thus, the compositions-of-matter having a co-encapsulated antibiotic agent according to some embodiments of the present invention can be used in a method of treating a medical condition associated with a pathogenic microorganism and further associated with an emergence of antimicrobial resistance in a subject still suffering from that medical condition after being treated with an antibiotic agent. The method is effected by administering to that subject, following the treatment with the antibiotic agent and the emergence of antimicrobial resistance to the antibiotic agent, a cochleate encapsulating a polymer and an antibiotic agent, as described herein.

In essence, the antibiotic agent is re-administered (administered again after the microorganism(s) developed resistance) to the subject in the form of a co-encapsulating cochleate, with the distinction that the pathogenic microorganism is now re-sensitized towards the antimicrobial agent by the polymer. Essentially, the two components, namely the antibiotic agent and the polymer, are administered concomitantly to the subject.

The phrase "antimicrobial re-sensitizing activity", as used herein in the context of the polymers according to the embodiments presented herein, defines a characteristic of the polymer which is related to three entities, namely (i) the polymer, (ii) an antibiotic agent, and (iii) a microorganism which became or may become resistant to the antibiotic agent in the sense that the microorganism is no longer sensitive to the antibiotic agent. Thus, the existence on an antimicrobial re-sensitizing activity allows the polymer to endow potency to, potentiate or re-potentiate the antibiotic agent against the microorganism by re-sensitizing the microorganism to the antibiotic agent.

By "re-sensitizing", it is meant that a microorganism that was sensitive (susceptible) to a treatment with antibiotic agent and became resistant to such a treatment, is turned again to be sensitive (susceptible) to such a treatment.

As used herein, the phrase "re-sensitizing effective amount" describes an amount of the antimicrobial re-sensitizing polymer, which is sufficient to reverse the emerged resistance towards the antibiotic agent.

In some embodiments, this phrase describes an amount of the polymer which is sufficient to reverse, or prevent, the emergence of resistance in the pathogenic microorganism causing the medical condition.

In the context of some embodiments of the present invention, the phrase "therapeutically effective amount" describes an amount of an active agent being administered, which will relieve to some extent one or more of the symptoms of the condition being treated. In the context of the present embodiments, the phrase "therapeutically effective amount" describes an amount of an antibiotic agent (including an antimicrobial polymer) being administered and/or re-administered in the form of a co-encapsulating cochleate, which will relieve to some extent one or more of the symptoms of the condition being treated.

In the context of medical conditions associated with a pathogenic microorganism, a therapeutically effective amount is at a level that is harmful to the target microorganism(s), namely a bactericidal level or otherwise a level that inhibits the microorganism growth or eradicates the microorganism.

It should be noted herein that a re-sensitizing effective amount with respect to the polymer, according to embodiments of the present invention, or any other agent, is substantially different than a therapeutically effective amount of the same agent in the sense that a re-sensitizing effective amount is not expected to be sufficient to cause destruction or disruption to the life-cycle of the target microorganism(s) when used exclusively, without the presence of another antibiotic agent. The polymer may have an antimicrobial activity by its own virtue, or lack such activity altogether.

In some embodiments, the polymer as described and used herein, has an antimicrobial therapeutic activity. A re-sensitizing effective amount of such a therapeutically active polymer is typically lower than the therapeutically effective amount of that polymer when used as an antimicrobial agent against the microorganism causing the condition to be treated.

Thus, according to some embodiments of the invention, the re-sensitizing effective amount of a polymer is lower than the therapeutically effective amount of this polymer with respect to the microorganism to be eradicated if/when the polymer is administered by itself per-se.

The efficacy of an antibiotic agent is oftentimes referred to in minimal inhibitory concentration units, or MIC units. A MIC is the lowest concentration of an antimicrobial agent, typically measured in micro-molar ($\mu$M) or micrograms per milliliter ($\mu$g/ml) units, that can inhibit the growth of a microorganism after a period of incubation, typically 24 hours. MIC values are used as diagnostic criteria to evaluate resistance of microorganisms to an antimicrobial agent, and for monitoring the activity of an antimicrobial agent in question. MICs are determined by standard laboratory methods, as these are described and demonstrated in the Examples section that follows. Standard laboratory methods typically follow a standard guideline of a reference body such as the Clinical and Laboratory Standards Institute (CLSI), British Society for Antimicrobial Chemotherapy (BSAC) or The European Committee on Antimicrobial Susceptibility Testing (EUCAST). In clinical practice, the minimum inhibitory concentrations are used to determine the amount of antibiotic agent that the subject receives as well as the type of antibiotic agent to be used.

As presented in the Examples section that follows, the polymers described herein exhibit MIC values per-se in the range of 3-7 $\mu$M. However, as antimicrobial re-sensitizing agents, the polymers described herein can be used effectively at as low as one quarter of these concentrations.

Thus, in some embodiments, a re-sensitizing effective amount of a polymer administered as a polymer-mediated cochleate as described herein, ranges from 1 MIC to ⅛ MIC. In some embodiments, the re-sensitizing effective amount ranges from ½ MIC to ¼ MIC.

When the co-encapsulated bioactive agent is an anticancerous agent, the composition-of-matter according to some embodiments of the present invention preferably uses a polymer which exhibits an anticancerous activity, and the composition-of-matter is then identified for use in treating cancer. In such cases, the bodily site to which the anticancerous agent(s) are delivered is the organ or tissue exhibiting the targeted tumors. In some embodiments, the cancer is MDR cancer.

In view of the above-described pharmaceutical activities exhibited by the compositions-of-matter described herein, according to other aspects of embodiments of the present invention there are provided methods and uses that utilize the compositions-of-matter described herein.

Hence, according to another aspect of embodiments of the present invention, there is provided a method of treating a medical condition associated with a pathogenic microorganism, which is effected by administering to a subject in need thereof a therapeutically effective amount of the composition-of-matter according to some embodiments of the present invention, or the pharmaceutical composition according to some embodiments of the present invention.

As discussed hereinabove, when the pathogenic microorganism is a resistant microorganism, the method is being for sensitizing or re-sensitizing the microorganism to an antibiotic agent. The antibiotic agent can be administered as a separate formulation, or be co-encapsulated in the polymer-mediated cochleate according to some embodiments of the present invention.

Medical conditions associated with a pathogenic microorganism include infections, infestation, contaminations and transmissions by or of pathogenic microorganism. In general, a disease causing infection is the invasion into the tissues of a plant or an animal by pathogenic microorganisms. The invasion of body tissues by parasitic worms and other higher pathogenic organisms is commonly referred to as infestation.

Invading organisms such as bacteria produce toxins that damage host tissues and interfere with normal metabolism; some toxins are actually enzymes that break down host tissues. Other bacterial substances may inflict their damage by destroying the host's phagocytes, rendering the body more susceptible to infections by other pathogenic microorganisms. Substances produced by many invading organisms cause allergic sensitivity in the host. Infections may be spread via respiratory droplets, direct contact, contaminated food, or vectors, such as insects. They can also be transmitted sexually and from mother to fetus.

Diseases caused by bacterial infections typically include, for example, actinomycosis, anthrax, aspergillosis, bacteremia, bacterial skin diseases, *bartonella* infections, botulism, brucellosis, *burkholderia* infections, *campylobacter* infections, candidiasis, cat-scratch disease, chlamydia infections, cholera, *clostridium* infections, coccidioidomycosis, cryptococcosis, dermatomycoses, diphtheria, ehrlichiosis, epidemic louse borne typhus, *Escherichia coli* infections, *fusobacterium* infections, gangrene, general infections, general mycoses, gonorrhea, gram-negative bacterial infections, gram-positive bacterial infections, histoplasmosis, impetigo, *klebsiella* infections, legionellosis, leprosy, leptospirosis, *listeria* infections, lyme disease, malaria, maduromycosis, melioidosis, mycobacterium infections, mycoplasma infections, necrotizing fasciitis, *nocardia* infections, onychomycosis, ornithosis, pneumococcal infections, pneumonia, pseudomonas infections, Q fever, rat-bite fever, relapsing fever, rheumatic fever, *rickettsia* infections, Rocky-mountain spotted fever, *salmonella* infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, *vibrio* infections, yaws, *yersinia infections, Yersinia pestis* plague, zoonoses and zygomycosis.

According to yet another aspect of embodiments of the invention, there is provided a method of delivering a bioactive agent to a bodily site of a subject in need thereof, which is effected by administering to the subject the composition-of-matter according to some embodiments of the present invention.

Following are some exemplary compositions-of-matter comprising a co-encapsulated bioactive agent according to some embodiments of the present invention, noted according to the bioactive agent that requires protection from degradative factors in physiological system and/or controlled rate of release, and its designated bodily site.

For example, the co-encapsulated bioactive agent can be a drug which is required for systemic distribution in the subject, such as the non-limiting examples of antibiotic agents, anti-pruritic agents, anesthetic drugs, vitamins, anti-oxidants, antihistamines and the likes.

Suitable antipruritic agents include, without limitation, methdilazine and trimeprazine.

Non-limiting examples of anesthetic drugs that are suitable for use in context of the present invention include lidocaine, bupivacaine, chlorprocaine, dibucaine, etidocaine, mepivacaine, tetracaine, dyclonine, hexylcaine, procaine, cocaine, ketamine, pramoxine and phenol.

Suitable antibiotic agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

For a non-limiting example, the co-encapsulated bioactive agent can be a steroidal or non-steroidal anti-inflammatory agent that requires local distribution in the subject to the site of the inflammation or inflamed tissue or organ.

Representative examples of non-steroidal anti-inflammatory agents that are usable in this context of the present invention include, without limitation, oxicams, such as piroxicam, isoxicam, tenoxicam, sudoxicam, and CP-14,304;

salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

For a non-limiting example, the co-encapsulated bioactive agent can be a chemotherapeutic agent that requires local distribution in the subject to the site of the tissue or organ to be treated.

Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

For a non-limiting example, the co-encapsulated bioactive agent can be hormones or antidepressant that requires distribution in the CNS of the subject. Hormones such as androgenic compounds and progestin compounds may also require local delivery.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin- and-noradrenaline-reuptake inhibitors ("SNFIs"), corticotropin-releasing factor (CRF) antagonists, α-adrenoreceptor antagonists, NK1-receptor antagonists, 5-HT$_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Accordingly, there is provided a use of the composition-of-matter according to some embodiments of the present invention in the preparation of a medicament for the treating a medical condition in a subject, as described herein.

An advantage of the cochleates according to some embodiments of the present invention is the stability of the composition-of-matter thereof. Thus, the compositions-of-matter presented herein can be administered orally, topically or by instillation, as well as by other routes, such as intravenous, subcutaneous, intraperitoneal, intradermal, intramuscular, intrathecal and the like routes.

In the context of many therapeutic methods and uses, a direct application of the composition-of-matter to mucosal surfaces is attractive particularly as a mean of drug delivery, and further particularly attractive in the context of stimulating an immune response to a co-encapsulated agent in the cochleate.

Pharmaceutical Compositions:

In any of the methods and uses described herein, the compositions-of-matter can be utilized either per se or as a part of a pharmaceutical composition which further comprises a pharmaceutically acceptable carrier.

As used herein the phrase "pharmaceutical composition" or the term "medicament" refer to a preparation of the antimicrobial re-sensitizing polymer described herein, with other chemical components such as pharmaceutically acceptable and suitable carriers and excipients, and optionally with additional active agents, such as an antimicrobial agent. The purpose of a pharmaceutical composition is to facilitate administration of a compound to a subject.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Pharmaceutical compositions for use in accordance with embodiments of the invention thus may be formulated in conventional manner using one or more pharmaceutically acceptable carriers comprising excipients and auxiliaries, which facilitate processing of the polymers and antimicrobial agents into preparations which can be used pharmaceutically. Proper formulation is dependent upon the route of administration chosen. Toxicity and therapeutic efficacy of the antimicrobial agents and re-sensitizing efficacy of the polymers described herein can be determined by standard pharmaceutical procedures in experimental animals, e.g., by determining the EC50, the IC50 and the LD50 (lethal dose causing death in 50% of the tested animals) for a subject combination of antimicrobial agent(s) and polymer(s). The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1). In general, the dosage is related to the efficacy of the active ingredient which, in the context of embodiments of the invention, is related to its minimal inhibitory concentration (MIC) and the particular pharmacokinetics and pharmacology thereof for absorption, distribution, metabolism, excretion and toxicity (ADME-Tox) parameters. For antimicrobial agents, a therapeutically effective amount is oftentimes about ten-fold the MIC of the antimicrobial agent. The re-sensitization effective amount for a polymer may be a low as equal or less than one MIC unit.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a polymer, either alone or in combination with a bioactive agent as described herein (e.g., an antibiotic or an anticancerous drug), formulated in a compatible pharmaceutical carrier may also be prepared, placed in an appropriate container, and labeled for treatment of an indicated condition, as is detailed herein.

It is expected that during the life of a patent maturing from this application many relevant OAK-mediated cochleates will be developed and the scope of the phrase "antibiotic delivery and potentiating vehicles" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Materials and Experimental Methods

Abbreviations (Lipids are Sorted Alphabetically)

CL, cardiolipin, 1,3-bis(sn-3'-phosphatidyl)-sn-glycerol;

DMPC, 1-2-dimyristoyl-phosphatidylcholine, a zwitterionic phosphatidylcholine;

DMPE, 1-2-dimyristoyl-phosphatidylethanolamine, a zwitterionic phosphatidylethanolamine;

DMPG, 1-2-dimyristoyl-phosphatidylglycerol, an anionic (negatively charged) phosphatidylglycerol;

DOPE, 1-2-dioleoyl-phosphatidylethanolamine, a zwitterionic phosphatidylethanolamine;

DOPG, 1-2-dioleoyl-phosphatidylglycerol, an anionic (negatively charged) phosphatidylglycerol;

DPPE, 1-2-dipalmitoyl-phosphatidylethanolamine a zwitterionic phosphatidylethanolamine;

PE, phosphatidylethanolamine, a family of zwitterionic lipids;

PG, phosphatidylglycerol, a family of anionic lipids;

POPC, 1-2-palmitoy-oleoyl-phosphatidylcholine a zwitterionic phosphatidylcholine;

POPE, 1-palmitoyl-2-oleoyl-phosphatidylethanolamine, a zwitterionic phosphatidylethanolamine;

TMCL, tetramyristoyl-cardiolipin, an anionic diphosphatidylglycerol;

TOCL, tetraoleoyl-cardiolipin, an anionic diphosphatidylglycerol.

AMPs, antimicrobial peptides; CFU, colony-forming unit; FIC, fractional inhibitory concentration; HDP, host-defense peptides; Fmoc, N-(9-fluorenyl)methoxycarbonyl; Laurdan, 6-dodecanoyl-2-dimethylaminonaphthalenelaurdan; LB, Luria Bertani; MDR, multidrug resistance; MIC, minimal inhibitory concentration; MLVs, multilamellar vesicles; OAK, oligo-acyl-lysyl; and PBS, phosphate-buffered saline.

Phospholipids:

Phospholipids were purchased from Avanti Polar Lipids (Alabaster, Ala., USA).

Chemical Syntheses and Analysis of Oak Polymers:

The polymers were produced by the solid phase method following methodologies disclosed in U.S. Pat. No. 7,504,381, WO 2006/035431, WO 2008/132738, WO 2009/090648 and U.S. Patent Application Nos. 20070032428 and 20100120671, all of which are incorporated by reference as if fully set forth herein.

Briefly, the polymers were synthesized while applying the Fmoc active ester chemistry on a fully automated, programmable peptide synthesizer (Applied Biosystems 433A). After cleavage from the resin, the crude product was extracted with 30% acetonitrile in water and purified by RP-HPLC (Alliance Waters), so as to obtain a chromatographic homogeneity higher than 95%. HPLC runs were typically performed on $C_{18}$ columns (Vydac, 250 mm×4.6 or 10 mm) using a linear gradient of acetonitrile in water (1% per minute), both solvents containing 0.1% trifluoroacetic acid. The purified polymers were subjected to mass spectrometry (ZQ Waters) and NMR analyses to confirm their composition, and stored as a lyophilized powder at −20° C. Prior to being tested, fresh solutions were prepared in water, vortexed, sonicated, centrifuged and then diluted in the appropriate medium.

Non Polymer Antimicrobial Agents (Antibiotics):

In order to demonstrate the sensitizing and re-sensitizing activity of the OAK polymers according to some embodiments of the invention, sensitive (susceptible) and resistant bacterial strains were tested for their response to several non-polymer antimicrobial agents, such as oxacillin, piperacillin, penicillin G, clarithromycin, ciprofloxacin, rifampicin, erythromycin, tetracycline and gentamicin.

Bacterial Strains:

Antibacterial activity was determined using the following strains of E. coli: 14182, 14384, U-16329 and U-16327; AG100, wild type (efflux+); AG100A, ΔacrAB (efflux−); AG100/ks, over-expressing β-lactamases; AB301, wild type (efflux+); and N281, having a ribosomal mutation.

Antibacterial Assays:

All bacteria were cultured in Luria-Bertani (LB) medium (10 g/l tryptone, 5 g/l yeast extract, 5 g/l NaCl, pH 7.4).

Minimal inhibitory concentration (MIC) was determined by microdilution assay in sterilized 96-well plates in a final volume of 200 µl. Bacteria were grown overnight in LB growth medium and diluted 10,000-fold in same medium. A 100 µl of LB containing bacteria (2-4×105 CFU/ml) were added to 100 µl of culture medium containing the test compound (0-110 µg/ml of an OAK polymer or 0-512 µg/ml of an antibiotic agent in serial two-fold dilutions).

Inhibition of proliferation was determined by optical density measurements (620 nm) after incubation overnight at 37° C.

Chemo-sensitization was assessed similarly, except that bacteria were incubated with a mixture of OAK and antibiotic (0-512 µg/ml in serial two-fold dilutions).

Synergistic effect of the combinations was assessed by determination of the fractional inhibitory concentration (FIC) where FIC=(MIC OAK in combination with antibiotic)/(MIC OAK alone)+(MIC antibiotic in combination)/(MIC antibiotic alone). Synergy was determined for FIC 0.5.

To assess bactericidal kinetics, bacterial suspensions were added to culture medium containing zero or various OAK concentrations (alone or in the presence of 16 µg/ml of erythromycin). Bacteria were sampled at various time intervals, subjected to serial 10-fold dilutions, and plated onto LB-agar. Cell counts were determined using the drop plate method. Plates were incubated overnight at 37° C. and colonies were counted.

Statistical data for each experiment were obtained from at least two independent assays performed in triplicate.

Ethidium Bromide (EtBr) Uptake Assay:

Cells were grown overnight in LB broth at 37° C. to an optical density of 1 (620 nm), washed twice in 200 µl PBS, and resuspended in the same buffer containing 0.5% glucose. After 10 minutes incubation at 37° C., samples were placed into a 96-well plate containing EtBr (final concentration 1.0 µg/ml) and mixed either with an OAK polymer, erythromycin or a combination of both. Fluorescence was recorded by a BioTeK synergy HT Microplate Reader (excitation, 530 nm; emission, 645 nm).

Formation of Cochleates in the Presence of an Oak Polymer:

Phospholipids were dissolved in a solution of chloroform: methanol (2:1), the solvent was then evaporated with a stream of nitrogen gas resulting in the dissolved lipid being deposited as a film on the test tube wall. Final traces of solvent were removed under vacuum for two hours. The lipid mixture used was 3 parts 1-palmitoyl-2-oleoyl phosphatidylethanolamine (POPE) with one part tetraoleoyl cardiolipin. The dry lipid film was then hydrated (final concentration 6.3 mM) and dispersed by vortexing with a solution of OAK in buffer (20 mM PIPES, 140 mM NaCl, 1 mM EDTA, pH 7.4 adjusted with NaOH) to produce a final suspension with a lipid to OAK molar ratio of 10. Co-encapsulation of OAK and erythromycin in cochleates was performed similarly except that the hydration step involved a solution containing both OAK and erythromycin in a ratio of 1:2 (w/w).

Sample Preparation for Structure Function Studies:

Lipid films containing binary mixtures of lipids were made from aliquots of stock solutions in chloroform:methanol (2:1). The solvent was evaporated with a stream of nitrogen gas and the lipids deposited as a film on the walls of a glass tube. The tubes were then placed in a vacuum dessicator for 3 hours. The films were kept under Argon at −20° C. The lipid films were hydrated with buffer solutions of OAK polymers with extensive vortexing, so as to have a lipid to polymer molar ratio of 10 to 1.

Light Microscopy:

Hydrated films were subjected to freeze thawing three times before imaging, to ensure proper equilibration of OAK with the multilamellar vesicles. A drop of this mixture was placed on a glass slide and covered with a glass coverslip. Light microscopy was carried out at room temperature using a Zeiss Axiovert 100M microscope with a Plan-Neofluar 100×/1.3 oil immersion objective. Images were analyzed with the Zeiss LSM image browser v2.8.

Freeze Fracture Electron Microscopy:

Samples were cryo-fixed using sandwich technique and liquid nitrogen-cooled propane (cooling rate of 20,000 Kelvin per second). The fracturing process was carried out in JEOL JED-9000 freeze-etching equipment and the exposed fracture planes were shadowed with Pt for 30 seconds in an angle of 25-35 degree and with carbon for 35 seconds (2 kV/60-70 mA, 1×10-5 Torr). The replicas produced this way were cleaned with concentrated, fuming $HNO_3$ for 24 hours followed by repeating agitation with fresh chloroform/methanol (1:1 by volume) at least 5 times. The replicas cleaned this way were examined at a JEOL 100 CX electron microscope.

Preparation of Multilamellar Vesicles (MLVs) for Laurdan Fluorescence:

Films of POPE:TOCL 75:25 were prepared from stock solutions in chloroform:methanol 2:1. The components were added in the appropriate proportions and the solvent dried first under nitrogen gas and then in a vacuum desiccator for 3 hours. The samples were kept under Argon at −20° C. When the probe Laurdan was present, it was incorporated into the films from a stock solution in methanol. Final lipid to Laurdan ratio was 1000. Films were hydrated with PIPES buffer pH 7.4 (20 mM PIPES, 140 mM NaCl, 1 mM EDTA) or with a buffer solution of OAK at a lipid to OAK ratio of 16, and vortexed extensively to prepare MLVs. Final concentration of MLVs was 2.5 mg/mL.

Laurdan Fluorescence Experiments:

Experiments were carried out at 37° C. in an Aminco Bowman SLM-II spectrofluorimeter equipped with temperature control and magnetic stirring. Quartz mirrored microcuvettes containing 250 µl of sample were used to measure fluorescence, exciting at 357 nm or at 386 nm and scanning emission in the range of 425-500 nm, or alternatively, setting emission at 440 nm or 490 nm and scanning excitation in the range of 320-410 nm, with a bandpass of 2 nm in excitation and 4 nm in emission. Generalized polarization was described by the equation: $GP=I440-I490/I440+I490$ where I440 and I490 are the intensities at 440 nm and 490 nm respectively, when exciting at 356 nm, or at 386 nm.

Assessment of Liposome Versus Cochleate Encapsulation:

Total and free OAK and/or antibiotic concentrations were evaluated by two methods. The MIC method was performed essentially as described above, except that the test compound was 0-20 µl of liposome or cochleate solution and subsequent serial two-fold dilutions.

Erythromycin-resistant *E. coli* strain (clinical isolate U-16327) and OAK-resistant *S. aureus* strain (clinical isolate 17314) were the indicator microorganisms for OAK (e.g., $C_{12}K$-$7\alpha_8$, SEQ ID NO: 3) and antibiotic (e.g., erythromycin) encapsulation efficiency, respectively. For total drug measurements, the liposomes were disintegrated by 0.1% v/v (final concentration) Triton X-100 prior MIC determination.

The outcome from this MIC method was verified by an assay based on the rapid reaction of fluorescamine with amino groups to produce fluorescent products. Briefly, 150 µl aliquots of samples (encapsulated OAK or Triton X-100 treated samples) and standards (0-100 µM of free OAK in serial two-fold dilutions) were pipetted into microplate wells. The microplate was placed on a microplate-shaker and 50 µl of 10.8 mM (3 mg/ml) fluorescamine dissolved in acetone were added to each well. Following the addition of fluorescamine the plate was shaken for one minute and fluorescence was recorded by a BioTeK synergy HT Microplate Reader (excitation, 360 nm; emission, 545 nm).

Whole Blood Assay:

Stability and drug release rates were assessed using the human blood-resistant *Klebsiella pneumoniae* CI 1286. Bacteria (50 µl containing $5\times10^6$ CFU/ml) and free or encapsulated OAK solutions in buffer (50 µl, final concentrations of 4 and 40 multiples of the MIC value) were added to 900 µl of whole blood. After the specified incubation periods (37° C.), aliquots were plated on LB agar as described above (Antibacterial assays) for CFU count.

In-Vivo Studies:

All animal studies were performed using male ICR mice (25±2 grams). Procedures, care and handling of animals were approved by the Technion Animal Care and Use committee. Maximal tolerated dose (MTD) was determined after single dose intravenous (IV) injections (0.18 ml in PBS) of free and encapsulated OAK. The systemic prevention of *E. coli*-induced mortality was assessed using neutropenic mice as described in the art. Infection was induced by intraperitoneal (IP) administration of a logarithmic-phase culture of *E. coli* (CI 14182) with mean bacterial inoculums $3\times10^7$ CFU in 0.3 ml PBS. One hour post inoculation mice were treated by a single IV injection of 0.18 ml vehicle (PIPES) alone (untreated control) or containing either free or encapsulated combinations as specified. Following the various treatments, animals were directly inspected for adverse effects for 4 hours and mortality was monitored for 6 days thereafter. Survival data were obtained from two independent experiments (n=8 per group per experiment).

Experimental Results

Previous studies, as well as U.S. Pat. No. 7,504,381, U.S. Patent Application Nos. 20070032428, 20100120671 and WO 2006/035431, have shown that the acyl-lysine antimicrobial polymers exert sequence dependant bacteriostatic and/or bactericidal effects with in-vitro MIC at low micromolar range and in-vivo efficacy at low mg/Kg range. WO 2009/090648 has shown that the OAK polymers exhibit antimicrobial re-sensitizing activities with respect to other antibiotics using bacterial cultures exposed to sub-MIC polymers concentrations, namely at concentrations wherein the polymers alone are not active, and shown that an effective re-sensitizing amount for the polymers is lower than their effective therapeutic amount, or MIC.

Presently it is shown that OAK polymers exert sensitization and re-sensitization of various pathogens to antibiotic activity in the form of a co-encapsulating cochleate. Thus, OAK polymers exhibit, according to embodiments of the present invention, at least a dual effect: promoting cochleate formation for producing encapsulated antibiotic agents and sensitizing a pathogen to the antibiotic activity. The OAKs' capacity to promote cochleate formation is exhibited over a wide range of lipid combinations, including mixtures which were know not to form cochleates hitherto, and/or lipid combinations which were know not to form cochleates without the presence of multi-valent metal ions.

Exemplary Polymers Library:

Several representative polymers according to the present embodiments, which are substantially comprised of a plurality of fatty acid (acyl) residues, lysine residues and ω-amino-fatty acid residues, also referred to herein and elsewhere as oligo-acyl-lysines or OAKs, were prepared according to the general procedure described in U.S. Pat. No. 7,504,381, U.S. Patent Application Nos. 20070032428, 20100120671 and WO 2006/035431, WO 2008/072242 and WO 2008/132738, and are presented in Table 1 below. The polymers in this section can be described using the shorthand denotations described below.

N or $NH_2$ (used herein interchangeably), when present, denotes an amino group, which may be a terminal group such as in a primary amine at the N-terminus of the polymer or a part of an amide at the C-terminus of the polymer, and may be a part of the peptide bond connecting two polymer residues;

The polymer unit $NC_{i(y)}$ denotes an ω-amino-fatty acid moiety, and polymer unit $C_{i(y)}$ denotes a fatty acid moiety, whereby i denotes the number of carbon atoms in the aliphatic chain thereof and (y) denotes a double bond along the chain, e.g. for $NC_{12(5-ene)}$, i is 12 and (y) is (5-ene) and the moiety is 12-amino-5-dodecenoic acid, whereby when the denotation (y) is absent, it is meant that the chain is saturated, e.g. $C_{12}$ denotes a lauric acid moiety;

The polymer unit K(x) denotes a lysine moiety, wherein (x) denotes the type of amine group in the amino acid which is used for conjugation with another unit in the polymer, whereby when the denotation (x) is absent, it is meant that conjugation is effected via the N-alpha of the lysine moiety and when (x) is (ε) it is meant that conjugation is effected via the epsilon amine of the lysine moiety;

The polymers presented herein and in U.S. Pat. No. 7,504,381, U.S. Patent Application Nos. 20070032428, 20100120671 and WO 2006/035431, WO 2008/072242 and WO 2008/132738, can be cyclic polymers, whereby the prefix "Cyclic-" is added to the denotation to mark a cyclic polymer. When cyclic, the polymer's termini form a linking moiety. For example, the linking moiety can be a peptide bond which forms between a terminal amine of an ω-amino-fatty acid moiety and a terminal carboxyl of a lysine moiety.

These exemplary polymers are referred to in this section according to the following formula:

T[NC$_i$K(x)]$_j$G or Cyclic-T[NC$_i$K(x)]$_j$G

In this formula, $NC_i$ or $NC_{i(y)}$ denotes an ω-amino-fatty acid moiety (an exemplary hydrophobic moiety according to the present invention, represented by $D_1 \ldots D_n$ in the general formulae I and II described herein); K(x) denotes a lysine moiety (an exemplary amino acid residue according to the present invention, denoted as $A_1 \ldots A_n$ in the general Formulae I and II described herein, such that [NC$_i$K(x)] denotes an ω-amino-fatty acid-lysine conjugate unit (denoted as [$A_1$-$Z_1$-$D_1$] ... [An-Zn-Dn] in the general Formulae I and II described herein); j denotes the number of the repeating units of a specific conjugate in the polymer (corresponding to n in the general Formulae I and II described herein); and T and G each independently denotes either a hydrogen (no denotation), a lysine moiety (denoted K), an amidated lysine moiety (denoted $KNH_2$), an ω-amino-fatty acid moiety (denoted $NC_i$ or $NC_{i(y)}$), a fatty acid moiety (denoted $C_i$ or $C_{i(y)}$), an ω-amino-fatty acid-lysine conjugate unit (denoted $NC_iK$ or $NC_{i(y)}K$), a fluorenylmethyloxycarbonyl moiety (denoted Fmoc), a benzyl moiety (denoted Bz), a tert-butylcarbonyl moiety (denoted t-Boc or Boc), an amine group (typically forming an amide at the C-terminus and denoted $NH_2$), and free acid group (for the C-terminus no denotation), an alcohol group, and any combination thereof (all corresponding to X and Y in the general Formula I described herein).

Thus, for example, a polymer according to embodiments of the present invention which is referred to herein as $C_{12}K(NC_8K)_7NH_2$ (SEQ ID NO: 3), corresponds to a polymer having the general Formula I described hereinabove, wherein: X is a conjugate of a fatty acid having 12 carbon atoms (lauric acid) and lysine; n is 6; $A_1 \ldots A_6$ are each a lysine moiety; $D_1 \ldots D_7$ are each an ω-amino-fatty acid having 8 carbon atoms (8-amino-caprylic acid); $Z_1 \ldots Z_7$ and $W_0$-$W_7$ are all peptide bonds; and Y is an amine. For clarity, the chemical structure of $C_{12}K(NC_8K)_7NH_2$ (SEQ ID NO: 3) is presented in Scheme 1 below:

Scheme 1

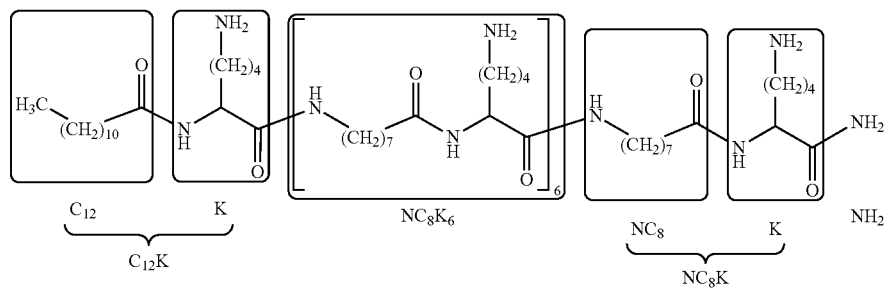

Table 1 below presents the exemplary polymers comprising a plurality of lysine moieties and ω-amino-fatty acid and fatty acid (acyl) moieties, referred to herein interchangeably (particularly in the Figures) as oligo-acyl-lysines or OAKs, according to some embodiments of the present invention, which were tested for their capacity to induce and support the formation of cochleates from various lipids. The table also notes the identification of each OAK polymer in two denotation formats and a reference and the former corresponding SEQ ID NO of the polymer if it was previously presented.

"Q" represents the overall molecular charge at physiological pH; "ACN (%)" represents the percent of acetonitrile in the HPLC-RP gradient mobile phase at which the polymer was eluted and which corresponds to the estimated hydrophobicity of the polymer. The column headed by "Ref." indicates prior reference of the OAK if present, wherein a number in parentheses "(##)" corresponds to the SEQ ID NO in U.S. Pat. No. 7,504,381; the letter "R" indicates a polymer published in Radzishevsky I. S. et al. (2008), Chem. Biol., 15(4), pp. 354-362; and "New" indicates a novel polymer disclosed herein.

TABLE 1

| SEQ ID NO | Polymer sequence | Alternative detonation | Q | ACN (%) | MIC E. coli (μM) | MIC A. aureus (μM) | Ref. |
|---|---|---|---|---|---|---|---|
| 1 | $C_{12}K(NC_8K)_5NH_2$ | $C_{12}K-5\alpha_8$ | 6 | 49.7 | 3.1 | 50 | (43) |
| 2 | $C_{12}K(NC_8K)_6NH_2$ | $C_{12}K-6\alpha_8$ | 7 | 50 | 3.1 | 50 | (44) |
| 3 | $C_{12}K(NC_8K)_7NH_2$ | $C_{12}K-7\alpha_8$ | 8 | 47.5 | 3.1 | 50 | (45) |
| 4 | $C_{12}K(NC_8K)_8NH_2$ | $C_{12}K-8\alpha_8$ | 9 | 48.5 | 3.1 | >50 | R |
| 5 | $C_{12}K(NC_8K)_9NH_2$ | $C_{12}K-9\alpha_8$ | 10 | 48.4 | 6.25 | >50 | R |
| 6 | $C_{12}K(NC_8K)_{11}NH_2$ | $C_{12}K-11\alpha_8$ | 12 | 42.2 | 3.1 | >50 | New |
| 7 | $C_{12}K(NC_4K)_7NH_2$ | $C_{12}K-7\alpha_4$ | 8 | 45.2 | 12.5 | >50 | (21) |
| 8 | $NC_{12}K(NC_8K)_7NH_2\alpha_{12}-7\alpha_8$ | | 9 | 36.9 | 12.5 | 50 | (52) |
| 9 | $C_{12}K(NC_{12}K)_7NH_2$ | $C_{12}K-7\alpha_{12}$ | 8 | 55.2 | >50 | >50 | R |

Example 1

Re-Sensitizing Effect of Oak Polymers

In-Vitro Susceptibility Studies:

The MIC values of antibiotics in the absence or presence of sub-MIC $C_{12}K-7\alpha_8$ (SEQ ID NO: 3) are presented in Table 2 below.

Table 2 summarizes the minimal inhibitory concentration (MIC) of conventional antibiotics as determined in a checkerboard like fashion against four MDR clinical isolates of *E. coli*, in the presence of various concentrations of $C_{12}K-7\alpha_8$ (SEQ ID NO: 3) representing 0, ¼, ⅓ or ½ of its MIC value against these strains (MIC=6.9 μg/ml, predetermined independently). The data demonstrate the dose-dependent ability of C12K-7α8 (SEQ ID NO: 3) to enhance the potency of several antibiotics.

TABLE 2

Antibiotic MIC (μg/ml) in presence of OAK
OAK MIC = 6.9 μg/ml; ND—Not Determined

| Target | Antibiotic | E. coli Strain | None | +3.5 μg/ml (½ MIC) | +2.3 μg/ml (⅓ MIC) | +1.7 μg/ml (¼ MIC) |
|---|---|---|---|---|---|---|
| Cell-wall synthesis | Penicillin G | 14182 | >512 | >512 | >512 | >512 |
| | | 14384 | >512 | >512 | >512 | >512 |
| | | U-16329 | 256 | 128-256 | 256 | 256 |
| | | U-16327 | >512 | 512 | >512 | >512 |
| | Oxacillin | 14182 | >512 | >512 | >512 | >512 |
| | | 14384 | >512 | >512 | >512 | >512 |
| | | U-16329 | >512 | 512 | >512 | >512 |
| | | U-16327 | >512 | 512 | >512 | >512 |
| | Piperacillin | 14182 | 512 | 64 | >512 | >512 |
| | | 14384 | 256-512 | 128 | 256-512 | 256-512 |
| | | U-16329 | 256 | 64 | 128 | 128-256 |
| | | U-16327 | 256 | 64 | 128-256 | 256 |
| Protein synthesis | Erythromycin | 14182 | 128 | 4 | 16 | 32 |
| | | 14384 | 128 | 8 | 16 | 64 |
| | | U-16329 | 256 | 16 | 64 | 128 |
| | | U-16327 | 512 | 16 | 64 | 128 |
| | Clarithromycin | 14182 | 64 | 4 | 8 | 32 |
| | | 14384 | 64 | 1 | 4 | 16 |
| | | U-16329 | 128 | 16 | 32 | 64 |
| | | U-16327 | 128 | 0.5 | 8 | 64 |
| | Tetracycline | 14182 | 64 | 8 | 16-32 | 32 |
| | | 14384 | 256 | 32 | 64-128 | 128-256 |
| | | U-16329 | 128-256 | 32 | 128 | 128 |
| | | U-16327 | >512 | 32 | 256 | 512 |
| | Gentamycin | 14182 | 128 | 64-128 | 128 | 128 |
| | | 14384 | 4 | 2 | 2-4 | 4 |
| | | U-16329 | >512 | >512 | >512 | >512 |
| | | U-16327 | 4 | 1-2 | 2 | 4 |
| Nucleic acid synthesis | Rifampin | 14182 | 16 | 0.25 | 2 | 4 |
| | | 14384 | 8 | 0.03 | 0.06-0.13 | 1 |
| | | U-16329 | 16 | 1 | 2 | 4 |
| | | U-16327 | 8-16 | 0.25 | 1 | 2 |
| | Ciprofloxacin | 14182 | <0.03 | ND | ND | ND |
| | | 14384 | <0.03 | ND | ND | ND |
| | | U-16329 | 64 | 64 | 64 | 64 |
| | | U-16327 | 256 | 16 | 32-64 | 64-128 |

As can be seen in Table 2, the MIC values of most antibiotics were extensively lowered against all four strains (by up to 256 folds), with the exception of cell-wall synthesis inhibitors (penicillin, oxacillin or piperacillin), which were not significantly influenced by the OAK presence. It is noted that rifampicin, erythromycin and its derivative clarithromycin are intrinsically inefficient (i.e., regardless of resistance acquiring capacity) and consequently are not indicated for treating Gram-negative bacteria, normally, unlike tetracycline or ciprofloxacin. Noteworthy is also the finding that gentamycin (which belongs to the same group of ribosome inhibitor antibiotics) was not potentiated remarkably, and that one of the two strains that were resistant to ciprofloxacin (gyrase inhibitor) was appreciably affected by the OAK (the other two strains were not assessed being already highly sensitive).

Table 3 presents the fractional inhibitory concentration (FIC) indices calculated based on the results shown in Table 2 hereinabove. In the table ND denotes "not determined" and NS denotes "no synergy". "Pen G" denotes penicillin G; "Oxa" denotes oxacillin; "Pip" denotes piperacillin; "Ery" denotes erythromycin; "Clari" denotes clarithromycin; "Tetra" denotes tetracycline; "Genta" denotes gentamicin; "Rif" denotes rifampicin; and "Cipro" denotes ciprofloxacin.

It is noted that in cases where the MIC of the antibiotic alone was >512 μg/ml, the FIC indices could not be calculated, and that FIC index values between 1.0-2.0 indicate indifference effects, values between 0.5-1.0 indicate additive effects, and values of ≤0.5 indicate synergistic effects (marked in bold and underlined letters).

agent upon E. coli CI-14182, wherein the solid line represents changes in MIC of individual compounds when both drugs are present in combination, and the dashed line represents the hypothetical additive effect and the squares represent the MIC evolution for each drug.

As can be seen in FIG. 1, the experimental MIC plot had a well-pronounced concave character revealing synergy in action of OAK with some of the antibiotics.

These results, presented in Table 3 and FIG. 1, demonstrate that some OAKs have a potentiating effect towards antibiotics whose resistance mechanism thereagainst is mediated by efflux pumps.

Mechanistic Studies:

In order to be effective, intracellular-targeting antibiotics must accumulate within the cytoplasm at effective concentrations. Resistant bacteria commonly overproduce related membrane proteins that act as export or efflux pumps for the drug. The drug is pumped out faster than it can diffuse in, thereby keeping intra-bacterial concentrations at low and inefficient levels.

It was hypothesized by the present inventors that some of the OAK polymers which are known for their membrane destabilizing properties, such as $C_{12}K-7\alpha_8$ (SEQ ID NO: 3), may increase access of antibiotic agents into the pathogen's cells, thus allowing their accumulation near the target site.

To verify this hypothesis, erythromycin was selected as an exemplary antibiotic agent since its bacteriostatic mode of action (as opposed to the bactericidal activity of OAK) would enable distinction of individual effects upon combination.

TABLE 3

| E. coli Strain | FIC | | | | | | | | |
|---|---|---|---|---|---|---|---|---|---|
| | Pen G | Oxa | Pip | Ery | Clari | Tetra | Genta | Rif | Cipro |
| 14182 | NS | NS | 0.63 | _0.46_ | _0.46_ | _0.50_ | 1 | _0.46_ | ND |
| 14384 | NS | NS | 0.63 | _0.39_ | _0.39_ | 0.58 | 1 | _0.31_ | ND |
| U-16329 | 1 | NS | 0.75 | 0.56 | 0.58 | 0.58 | NS | _0.46_ | 1.5 |
| U-16327 | NS | NS | 0.63 | _0.46_ | _0.39_ | 0.56 | 0.75 | _0.38_ | _0.46_ |

As can be seen in Table 3, no antagonistic effect was obtained in any case (FIC ≥2.0). As can further be seen in Table 3, indifference or additive effects (FIC values between 1.0-2.0 and 0.5-1.0, respectively) were observed upon combinations with most antibiotics. Synergy (FIC ≤0.5) was obtained against at least one of the strains tested when combining sub-MIC OAK levels with the intracellular-targeting antibiotics (erythromycin, clarithromycin, tetracycline, rifampicin and ciprofloxacin).

Synergy is also evident when plotting the results as a fraction of MIC of individual compounds. Here, drugs are considered synergistic if the curve has a concave shape, whereas a linear plot reflects additive action of the drugs, and a convex graph is indicative of antagonistic interaction.

FIG. 1 presents comparative plots of MIC fraction of an exemplary antibiotic, erythromycin, versus the MIC fraction of an exemplary OAK, $C_{12}K-7\alpha_8$ (SEQ ID NO: 3), showing synergistic inhibitory activity of the OAK and the antibiotic For this purpose, isogenic pairs of E. coli K-12 strains including a resistant wild type (AG100) and its efflux knockout mutant (AG100A) as well as two control mutants, a β-lactamase over-expressing strain (AG100/ks), a ribosomal protein mutant and its wild-type strain (N281 and AB301, respectively), were selected as exemplary pathogenic targets.

It is noted herein that the OAK MIC value (predetermined independently) was similar for the mutant strains and the clinical isolates (data not shown).

The results are summarized in terms of FIC values and presented in Table 4.

Table 4 presents the FIC index for antibiotics activity in presence of sub-MIC levels of an exemplary OAK polymer $C_{12}K-7\alpha_8$ (SEQ ID NO: 3) against E. coli mutants, wherein "ND" denotes "not determined" and "NS" denotes "no synergy"; FIC indices could not be calculated where the MIC of the antibiotic alone was >512 μg/ml; FIC index values between 1.0-2.0 indicate indifference effects; values between 0.5-1.0 indicate additive effects; and values of ≤0.5 indicate synergistic effects (marked in bold and underlined letters).

TABLE 4

| E. coli Strain | Genotype | FIC | | | | | | | |
|---|---|---|---|---|---|---|---|---|---|
| | | Pen | Oxa | Pip | Ery | Clari | Tetra | Genta | Rif |
| AG100 | Wild type (efflux+) | 0.58 | 0.5 | 0.75 | 0.46 | 0.39 | 0.63 | 1.0 | 0.46 |
| AG100A | ΔacrAB (efflux−) | 1.0 | 0.75 | ND | 0.86 | 0.75 | 1.0 | 1.0 | 0.75 |
| AG100/ks | β-lactamases over-expressing | NS | NS | NS | ND | ND | ND | ND | ND |
| AB301 | Wild type (efflux+) | ND | ND | ND | 0.56 | 0.56 | ND | ND | ND |
| N281 | Ribosomal mutation | ND | ND | ND | 1.0 | 1.0 | ND | ND | ND |

As can be seen in Table 4, the OAK enhanced erythromycin potency only against the wild type strains. Moreover, the fact that higher potencies were obtained with β-lactam antibiotics against AG100 but not AG100/ks, suggests that the OAK can sensitize additional antibiotics whose resistance mechanism includes efflux pumps.

To corroborate the potential role of $C_{12}K$-$7\alpha_8$ (SEQ ID NO: 3) in assisting antibiotics accumulation inside bacteria, the intracellular accumulation of ethidium bromide (EtBr) was measured. Ethidium bromide is known for its ability to spontaneously translocate across bacterial membranes and interact with nucleic acids, as can be evidenced by the increase in fluorescence signal.

Figure 2A:
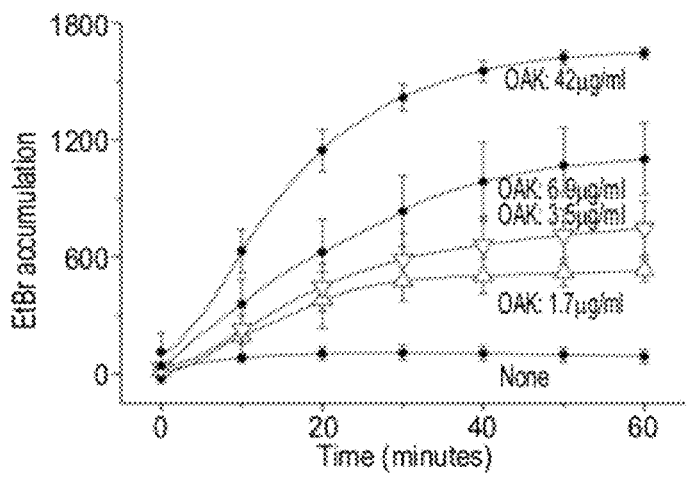
Figure 2B:
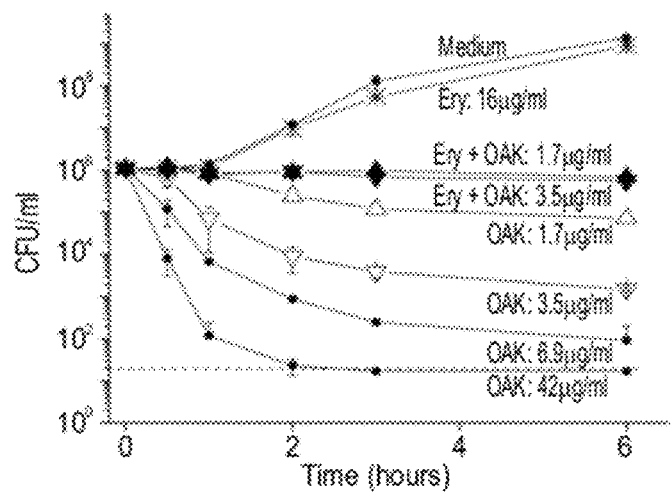
Figure 2C:
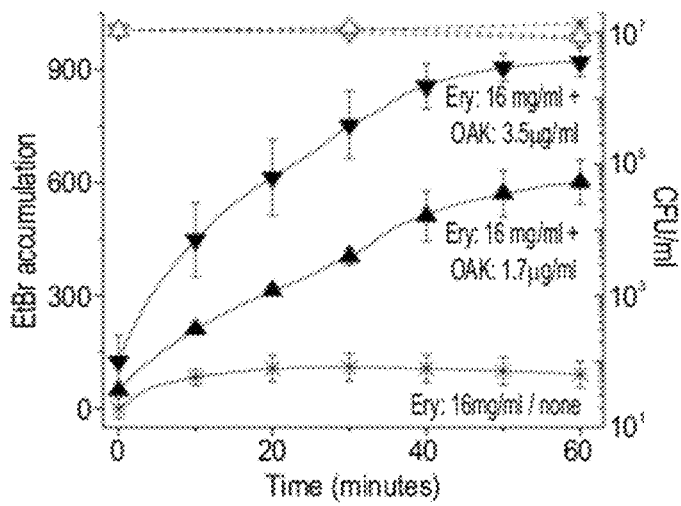

FIGS. 2A-C present comparative plots obtained in mechanistic studies of OAK/antibiotic synergy using E. coli AG100, wherein FIG. 2A presents data of the accumulation of EtBr in bacteria suspended in PBS in presence of the specified exemplary OAK concentrations, FIG. 2B presents data showing the viability upon exposure to the exemplary OAK alone, or combinations of the OAK and erythromycin (dashed line represents the limit of detection), and FIG. 2C presents data of EtBr accumulation upon exposure to erythromycin in the presence of sub-MIC levels of the exemplary OAK (marked in solid lines) and the corresponding time-kill curves (marked in dashed lines), whereas all data represent mean values±standard deviations obtained from at least two independent experiments performed in duplicates.

As can be seen in FIG. 2A, $C_{12}K$-$7\alpha_8$ (SEQ ID NO: 3) enhanced in a dose-dependent manner the otherwise slow and limited spontaneous EtBr uptake. As can be seen in FIG. 2B, time-kill experiments using $C_{12}K$-$7\alpha_8$ (SEQ ID NO: 3) showed that the OAK exerts significant bactericidal activity at sub-MIC concentrations, in concordance with FIG. 2A. However, when exposed simultaneously to sub-MIC values of both OAK and erythromycin, the mixture exerted an essentially bacteriostatic effect, supporting the view that upon combination, the OAK assisted erythromycin action and not the opposite. As can be seen in FIG. 2C, by combining both the time-kill experiment and the EtBr uptake assay, it appears that sub-MIC concentrations of the mixture have permeated bacterial cytoplasmic membrane, leading to drug accumulation inside of live bacteria.

Example 2

Oak-Mediated Cochleates

OAK-Mediated Formation of Cochleates:

Simultaneous delivery of both OAK and antibiotic in-vivo would allow assessing the synergistic effect of the OAK. Co-encapsulation of OAK and antibiotic would enable the synergistic drug interaction observed in-vitro to occur in-vivo as well. Hence, the aspect of facilitating the systemic and simultaneous delivery of both OAK and antibiotic to the infection site in animals was studied by forming phospholipid-based drug delivery systems which co-encapsulate both OAK and antibiotic. As discussed hereinabove, it was surprisingly found that OAK polymers afforded the formation of phospholipid-based cochleates.

Figure 3:
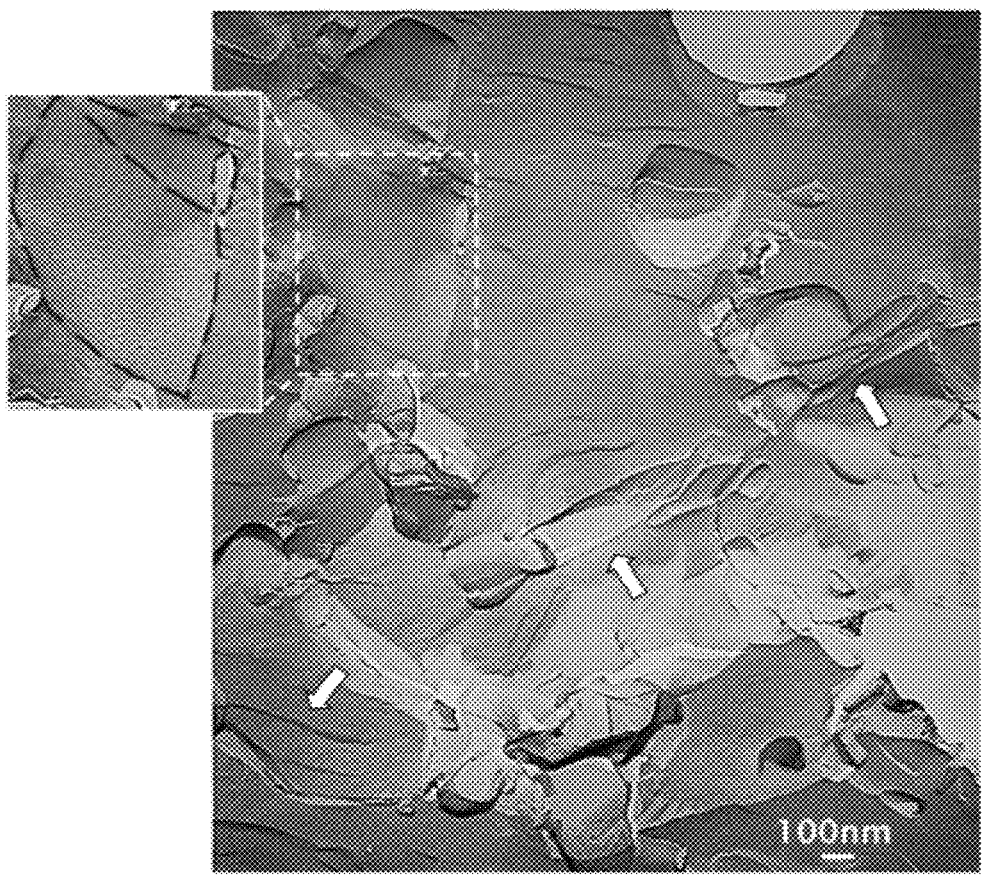
FIG. 3 presents a freeze-fracture electron-micrograph of an OAK-triggered formation of cochleate cylinders, composed of POPE:CL 75:25 (molar ratio), at an OAK to lipid molar ratio of 1:10, wherein the arrows point to some of the cochleates, and the inset shows a magnified premature cochleate cylinder at the edge of a bilayer sheet.

FIG. 3 presents a freeze-fracture electron-micrograph of an OAK-triggered formation of cochleate cylinders, composed of POPE:CL 75:25 mole equivalents, at an OAK to lipid molar ratio of 1:10, wherein the arrows point to some of the cochleates, and the inset shows a magnified premature cochleate cylinder at the edge of a bilayer sheet.

As shown in FIG. 3, under the influence of the exemplary OAK $C_{12}K$-$7\alpha_8$ (SEQ ID NO: 3), a massive liposome fusion was observed by freeze-fracture microscopy in the presence of MLVs of POPE:TOCL, including the formation of structures known as cochleate cylinders. At the specific conditions used, the cochleate cylinders formed under the influence of $C_{12}K$-$7\alpha_8$ (SEQ ID NO: 3) are not always fully developed and frequently noticeable at the rims of bilayer sheets just starting to roll up into cochleate cylinder. As can further be seen in the inset of FIG. 3, a cochleate cylinder is detectable in the upper part and a bilayer sheet, not rolled up yet, resembling a paper towel still hanging out from a paper-towel-roll.

Characterization of Cochleates by Laurdan Fluorescence:

The probe Laurdan, when localizes at the lipid interface, is sensitive to the polarity of the environment, and therefore Laurdan fluorescence has been proposed as a means to detect the formation of cochleates.

The method is based on observing changes in the fluorescence of the Laurdan probe that are consistent with a more dehydrated and rigid membrane interface being indicative of cochleate formation.

Figure 4A:
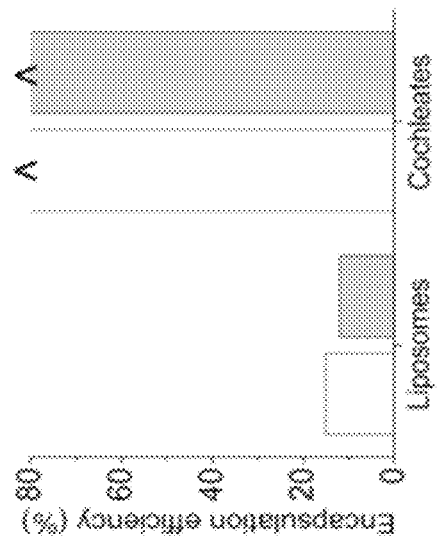
Figure 4C:
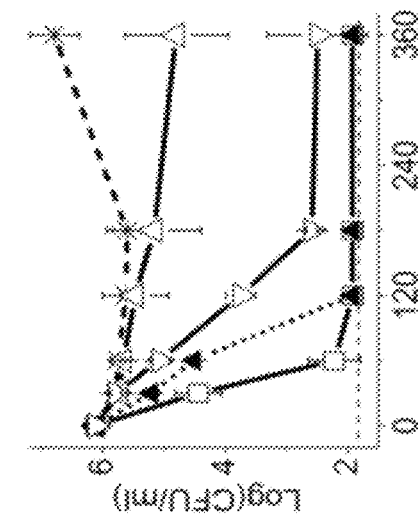
Figure 4B:
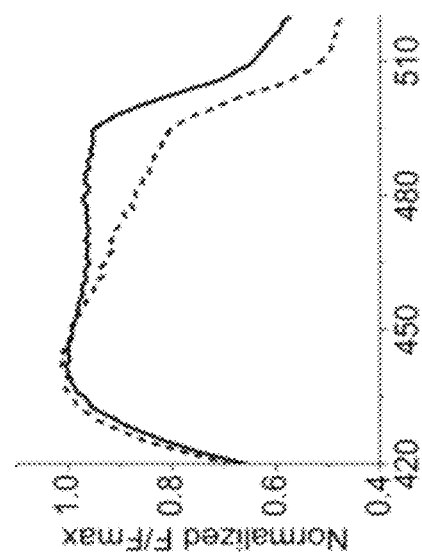
Figure 4D:
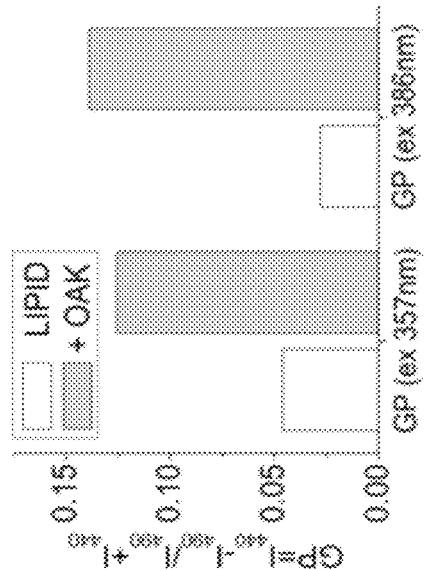

FIGS. 4A-D present various means of characterization of OAK-mediated cochleates, wherein FIG. 4A presents the relative fluorescence intensities observed when exciting at 356 nm for MLVs of POPE:TOCL 75:25 (2.5 mg/mL) in the absence (solid line) and presence (dashed line) of an exemplary OAK (at a lipid to OAK ratio of 16) in PIPES pH 7.4 (20 mM PIPES, 0.14 M NaCl, 1 mM EDTA) at 37° C., whereas F is the observed fluorescence at any wavelength and Fmax is the fluorescence of the maximum value observed at 440 nm, set to 1 to normalize the curves; FIG. 4B presents the generalized polarization, as described by the equation $GP=I_{440}-I_{490}/I_{440}+I_{490}$ where $I_{440}$ and $I_{490}$ are the intensities at 440 nm and 490 nm respectively, when exciting at 356 nm or at 386 nm, whereas the lower bars were obtained with MLVs of POPE:TOCL (2.5 mg/ml) and taller bars correspond to MLVS in the presence of OAK at the conditions described in panel A; FIG. 4C presents the OAK encapsulation efficiency in liposomes (PC:PEG2000) and cochleates (POPE:TOCL) as determined by MIC and fluorescamine methods (white and gray, respectively), whereas the symbol "^" indicates >80%; and FIG. 4D presents the time-kill curves of Klebsiella pneumoniae cultured in whole blood in presence of 4 and 40 multiples of the MIC value ("▲" black triangle and "▽" inverted white triangle, respectively) of cochleate-encapsulated or liposome-encapsulated OAK (empty symbols and solid lines versus filled symbols and dotted line, respectively), "*" asterisk marks the plot of normal bacterial growth, "□" rectangle marks the plot of free (non-encapsulated) OAK at 4 multiples of the MIC value.

As can be seen in FIGS. 4A-D, fluorescence results with MLVs of POPE:TOCL show the distinct pattern of cochleate formation in the presence of OAK, particularly when exciting at 357 nm (FIG. 4A). The lipid mixture itself is in the liquid crystalline state and it exhibits the two peaks characteristic of the liquid crystalline phase as detected by Laurdan fluorescence, at 440 and 490 nm. Addition of OAK produced a large decrease in the intensity at 490 nm and a small blue shift at 440 nm (best seen when exciting at 357 nm) (FIG. 4A). This indicates that the ground state of the probe was not stabilized by dipolar interactions with the solvent, as happens in the liquid crystalline state of the lipid mixture alone, and this reflects the dehydrated environment sensed by the probe in the cochleate cylinders. In addition, the generalized polarization of Laurdan (GP) in the lipid mixture was calculated with and without OAK (FIG. 4B), confirming the presence of cochleates forming instantaneously upon addition at room temperature of the exemplary OAK $C_{12}K$-$7\alpha_8$ (SEQ ID NO: 3) and characterized under physiological conditions of temperature and pH. When describing generalized polarization, a dramatic increase was observed in the presence of OAK (FIG. 4B), demonstrating that the formation of cochleates is facilitated by the presence of an OAK polymer.

Assessment of Encapsulated Drugs:

Encapsulation efficiencies were determined by analyzing the inhibitory effects against *E. coli* by the free (non-encapsulated) OAK fraction in cochleate preparations, assuming that cochleated OAK is inactive under the experimental conditions.

Based on this evaluation it was concluded that >80% of the OAK was bound. This result was validated using an assay based on the reaction of fluorescamine with amino groups, calibrated against the exemplary OAK $C_{12}K$-$7\alpha_8$ (SEQ ID NO: 3) standard curve (data not shown). For comparison, it was attempted to encapsulate the OAK within liposomes composed of the neutral lipid phosphatidylcholine (PC) and 1,2-distearoyl-sn-glycero-3-phosphoethanolamine-N-[polyethylene-glycol-2000] (PEG2000), known to increase liposome half-life in the circulation.

As can be seen in FIG. 4C, the encapsulation efficiency of the OAK in liposomes was significantly lower (<20%) compared to encapsulation in cochleates.

The stability of OAK-cochleate and OAK-liposome preparations in whole blood was compared by assessing antibacterial activity against the blood-resistant strain of *Klebsiella pneumonia*.

As can be seen in FIG. 4D, non-encapsulated OAK maintained rapid bactericidal activity at four multiples of the MIC value, as previously reported. The differential killing rates between free and encapsulated OAK suggested that most of the liposome-encapsulated OAK rapidly leaks out in contact with blood, whereas OAK release from cochleates was significantly slower. Also, the fact that killing rates by cochleates were slower than liposome-encapsulated OAK even at concentrations up to 40 times the MIC supports the notion of relatively superior stability of the OAK-cochleate system.

Thus, due to the poor encapsulation efficiency and blood stability in liposome, no further attempt was made to assess liposomal co-encapsulation.

Co-encapsulation of both OAK and erythromycin in cochleates was assessed essentially as described above, i.e., by using an erythromycin-resistant *E. coli* strain (clinical isolate U-16327) as the indicator organism for the exemplary OAK $C_{12}K$-$7\alpha_8$ (SEQ ID NO: 3), or the OAK-resistant *Staphylococcus aureus* strain (clinical isolate 17314) as the indicator for erythromycin encapsulation efficiency. It was concluded that erythromycin was efficiently encapsulated (>80%) and moreover did not alter OAK encapsulation (data not shown).

In-Vivo Studies:

Preliminary in-vivo experiments to assess potential benefits of OAK-induced cochleate co-encapsulation of antibiotic was performed as follows. To determine the maximal tolerated dose (MTD) the acute toxicity was compared by single IV administration of free and cochleate-encapsulated OAK. The MTD of free exemplary OAK $C_{12}K$-$7\alpha_8$ (SEQ ID NO: 3) was estimated at 5 mg OAK/kg of mouse weight (33% mortality was observed at 10 mg/kg) whereas MTD of the cochleated version is estimated at least 5-fold higher as no detectable signs of toxicity were apparent at 20 mg/kg (data not shown), indicating that encapsulation of $C_{12}K$-$7\alpha_8$ (SEQ ID NO: 3) has significantly reduced its toxicity. Systemic efficacy was assessed by monitoring mice survival after intraperitoneal inoculation followed with intravenous treatment (1 hour after inoculation). The outcome from a representative experiment where administration of each of the drugs alone was inefficient are presented in FIGS. 5A-B.

FIGS. 5A-B present comparative plots of the results of systemic efficacy studies in neutropenic mice, wherein FIG. 5A presents the survival experiment showing the individual contribution of erythromycin (5 mg/kg) or $C_{12}K$-$7\alpha_8$ (SEQ ID NO: 3) (5 mg/kg), whereas the mice (n=8/group) were inoculated IP with $3\times10^7$ cfu of *E. coli* (clinical isolate 14182) and treated 1 hour after infection by single IV administration of $C_{12}K$-$7\alpha_8$ (SEQ ID NO: 3) (free or cochleated) or free erythromycin; and FIG. 5B presents the survival rates of the infected mice (n=8/group) when treated by single IV administration of cochleates encapsulating both OAK and erythromycin.

As can be seen in FIGS. 5A-B, administration of co-encapsulated OAK and erythromycin has significantly increased mice survival in a dose-dependent manner (P-value <0.05).

Conclusions:

It has been shown hereinabove that co-encapsulation of OAK polymers and classical antibiotic drugs by means of cochleates constitute an appropriate means to effect synergistic action between antibiotics.

The results presented hereinabove provide evidence for the capacity of OAK polymers, such as the exemplary $C_{12}K$-$7\alpha_8$ (SEQ ID NO: 3), to enhance bacterial sensitivity to certain antibiotics, indicating that the OAK acts synergistically with antibiotics whose resistance mechanism is mediated by efflux pumps. The results presented hereinabove suggest that in presence of intracellular-targeting antibiotics, sub-MIC levels of the membrane-targeting OAK are sufficient to induce mild permeation of the cytoplasmic membrane, thereby facilitating "backdoor" entry of antibiotics that can now accumulate and efficiently attack their cytoplasmic target.

The fact that $C_{12}K$-$7\alpha_8$ (SEQ ID NO: 3) did not synergize with gentamycin (which also targets ribosomal RNA), does not necessarily contradict this hypothesis since the strategy that bacteria commonly use to neutralize this aminoglycoside antibiotic differs in that aminoglycosides are rather modified enzymatically, resulting in lower affinity for the target site. It is therefore probable that the OAK did not enhance the effect of gentamycin since it affects the membrane rather than the antibiotic-deactivating enzymes. As previously disclosed, membrane disruption effect and its ensuing bactericidal activity of OAK polymers, such as the exemplary $C_{12}K$-$7\alpha_8$ (SEQ ID NO: 3), was observed even at sub-MIC values (see, for example, FIGS. 6A-B).

The unexpected capacity of OAK polymers, such as $C_{12}K$-$7\alpha_8$ (SEQ ID NO: 3), to promote cochleate formation was demonstrated hereinabove. While the formation of cochleates from lipid bilayers has been known for some time, most studies have used calcium as a trigger for cochleate formation by phosphatidylserine.

Cochleates have attracted interest as particles that could serve as adjuvants for the enhancement of immune reactions as well as for drug delivery. Even oral drug delivery is considered and performed since cochleate cylinder are stable under acid conditions. The results presented hereinabove show that in the presence of a mixture of zwitterionic and anionic phospholipids (POPE:TOCL) the OAK formed rolled-up sheets, as shown in FIG. 3, which can be used for the entrapment and delivery of drugs. The formation of cochleates is especially surprising since divalent cations, needed to form cochleate cylinders from anionic lipids (usually phosphatidylserine), are potentially blocked by EDTA dissolved in the buffer, thus suggesting that the multiple positive charged OAK cause the cylinders formation, by substituting for the $Ca^{++}$ effect.

It has been shown hereinabove that the OAK-mediated cochleates have efficiently encapsulated erythromycin, as an exemplary antibiotic, thus forming a drug delivery system capable of delivering both drugs simultaneously. This constitutes a unique encapsulation method in that the OAK polymer enacts a passive role that drives cochleate formation, and at the same time enacts an active role destined to sensitize bacteria to a co-encapsulated antibiotic.

The in-vivo data provided strong evidence for the ability of this approach to achieve significant systemic therapeutic efficacy against an MDR strain of *E. coli*, as demonstrated by combining OAK and erythromycin. Among MDR bacteria, *E. coli* strains are especially concerning, owing to their increasing infection incidence, thus becoming predominant amongst extreme multi-resistant pathogens.

Unlike individual treatments with free erythromycin or cochleated OAK, the co-encapsulation of erythromycin in OAK-mediated cochleates can decrease drug toxicity and increase systemic therapeutic efficacy. Collectively, the data suggest a useful approach for combating efflux-enhanced drug resistance.

Example 3

Structure-Function Relationship of Oak Polymers in Cochleate Formation

While the formation of cochleates is not a common event, their formation has been observed as a consequence of the bridging of anionic lipid bilayers with $Ca^{2+}$. As discussed hereinabove, it has been reported that poly-L-Lysine and tobramycin can induce the formation of cochleates with small unilamellar vesicles (SUVs) of the lipid dioleoylphosphatidylserine [Syed et al., 2008] also in the presence of $Ca^{2+}$, but not with EDTA.

The experiments presented hereinbelow were designed to study some of the OAK's structural and chemical properties which affect cochleation.

Light Microscopy:

In order to optimize conditions for cochleate formation, a set of lipid mixtures were imaged by light microscopy in the presence of several different OAKs. These OAKs were chosen based on data obtained from light microscopy and from freeze-fracture electron microscopy of selected examples, which indicated that they presented a tendency to form cochleated structures.

Screening of the samples for cochleate formation was made by a comparison of the type of structures that were observed in the obtained light microscopy images versus light microscopy images reported in the literature [Syed et al., 2008, supra].

FIGS. 6A-C present a series of light microscopy photographs of samples having the exemplary OAK polymer $C_{12}K$-$7\alpha_8$ (SEQ ID NO: 3) with lipid mixture DMPE:TOCL 75:25 (FIG. 6A), DPPE:TOCL 75:25 (FIG. 6B) and DMPE:DOPG 75:25 (FIG. 6C), showing the formation of large cochleates.

FIGS. 7A-I present a series of light microscopy photographs of samples having a lipid composition of POPE:TOCL 75:25 and the exemplary OAK polymers $C_{12}K$-$5\alpha_8$ (SEQ ID NO: 1) in FIG. 7A, $C_{12}K$-$6\alpha_8$ (SEQ ID NO: 2) in FIG. 7B, $C_{12}K$-$7\alpha_8$ (SEQ ID NO: 3) in FIG. 7C, $C_{12}K$-$8\alpha_8$ (SEQ ID NO: 4) in FIG. 7D, $C_{12}K$-$9\alpha_8$ (SEQ ID NO: 5) in FIG. 7E, $C_{12}K$-$11\alpha_8$ (SEQ ID NO: 6) in FIG. 7F, $C_{12}K$-$7\alpha_4$ (SEQ ID NO: 7) in FIG. 7G, $\alpha_{12}$-$7a8$ (SEQ ID NO: 8) in FIGS. 7H and $C_{12}K$-$7\alpha_{12}$ (SEQ ID NO: 9) in FIG. 7I.

FIGS. 8A-D present a series of light microscopy photographs of samples having anionic lipid compositions devoid of zwitterionic lipids, showing crystal-like structures in POPG:TOCL 75:25 with $C_{12}K$-$7\alpha_8$ (SEQ ID NO: 3) in FIG. 8A or DMPG:TOCL 75:25 with $C_{12}K$-$5\alpha_8$ (SEQ ID NO: 1) in FIG. 8B, and mostly liposomes in DMPG:TOCL 75:25 with $C_{12}K$-$7\alpha_8$ (SEQ ID NO: 3) in FIG. 8C or with $C_{12}K$-$9\alpha_8$ (SEQ ID NO: 5) in FIG. 8D.

Figures 9A, 9B, 9C, 9D:
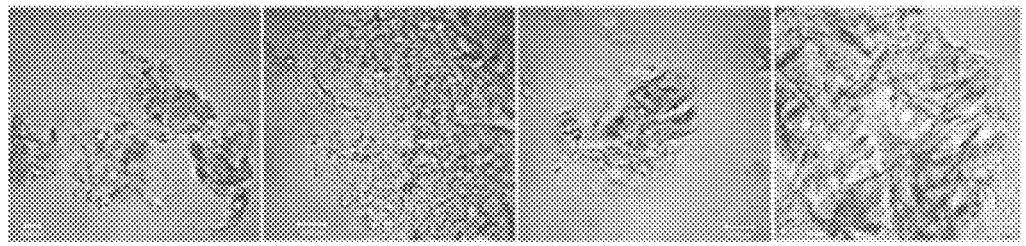
FIGS. 9A-E present a series of light microscopy photographs of samples showing cochleate needles formed from DMPE:TOCL 75:25 with $C_{12}K-7\alpha_8$ (SEQ ID NO: 3) in FIG. 9A, $C_{12}K-5\alpha_8$ (SEQ ID NO: 1) in FIG. 9B, $C_{12}K-8\alpha_8$ (SEQ ID NO: 4) in FIG. 9C, $C_{12}K-9\alpha_8$ (SEQ ID NO: 5) in FIG. 9D, and complete absence of cochleates with $C_{12}K-7\alpha_8$ (SEQ ID NO: 3) and DOPE:POPG:TOCL 80:15:5 in FIG. 9E.
Figure 9E:
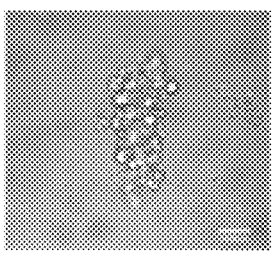

FIGS. 9A-E present a series of light microscopy photographs of samples showing cochleate needles formed from DMPE:TOCL 75:25 with $C_{12}K$-$7\alpha_8$ (SEQ ID NO: 3) in FIG. 9A, $C_{12}K$-$5\alpha_8$ (SEQ ID NO: 1) in FIG. 9B, $C_{12}K$-$8\alpha_8$ (SEQ ID NO: 4) in FIG. 9C, $C_{12}K$-$9\alpha_8$ (SEQ ID NO: 5) in FIG. 9D, and complete absence of cochleates with $C_{12}K$-$7\alpha_8$ (SEQ ID NO: 3) and DOPE:POPG:TOCL 80:15:5 in FIG. 9E.

Figures 10A, 10B:
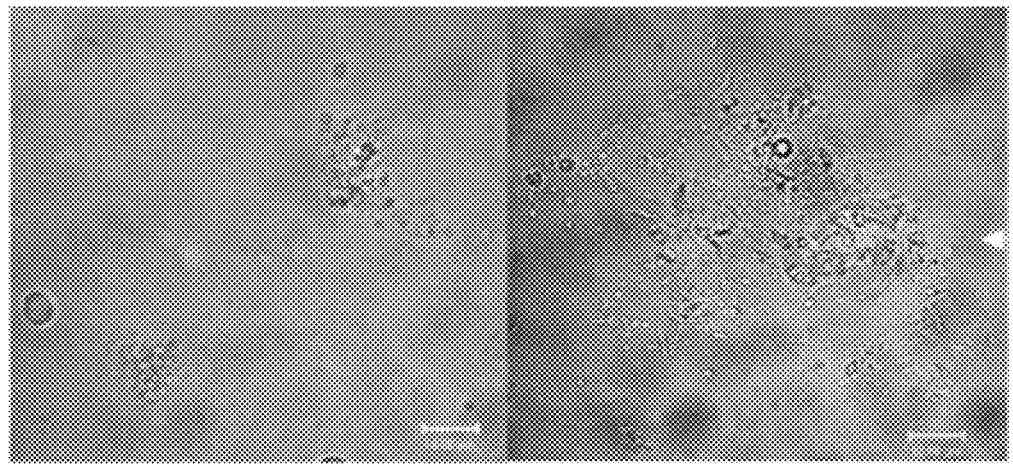
FIGS. 10A-B present a series of light microscopy photographs of samples of $C_{12}K-7\alpha_8$ (SEQ ID NO: 3) at a lipid to polymer ratio of 10 with POPE:TOCL 50:50 in FIG. 10A and with TOCL in FIG. 10B, showing few liposomes structures.
Figure 11A:
FIGS. 11A-J present a series of freeze-fracture electron micrographs of $C_{12}K-7\alpha_8$ (SEQ ID NO: 3) with DMPE:TOCL 75:25 referred to as "sample 2" (FIGS. 11A-C), DPPE:TOCL 75:25 referred to as "sample 3" (FIGS. 11D-F), DMPE:DOPG 75:25 referred to as "sample 5" (FIGS. 11G-H), POPG:TOCL 75:25 referred to as "sample 1" (FIG. 11I) and POPC:TOCL 75:25 referred to as "sample 4" (FIG. 11J), at a molar ratio of 10:1 lipid to polymer, wherein the bar represents 100 nm on all electron micrographs, shadow direction is cast bottom to top and white arrows mark some cochleate structures.
Figure 11B:
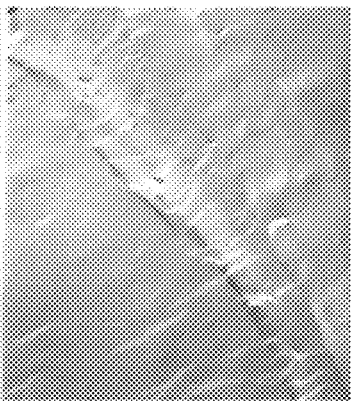
Figure 11C:
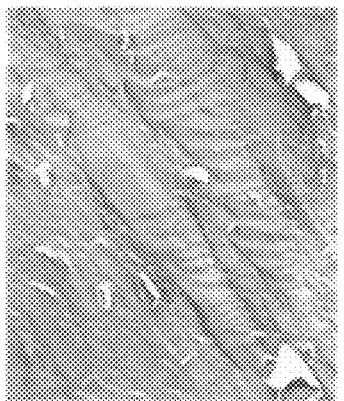
Figure 11D:
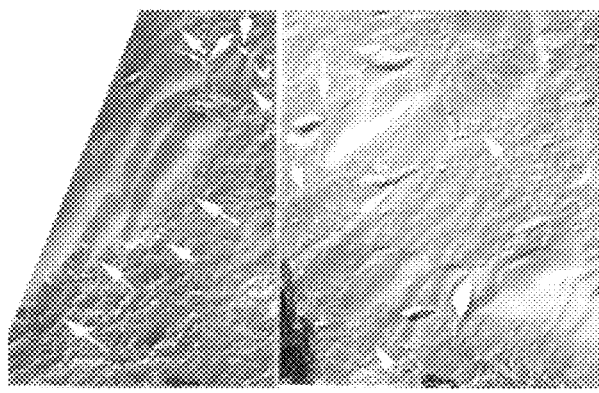
Figure 11E:
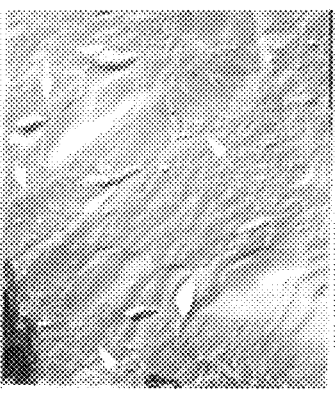
Figure 11F:
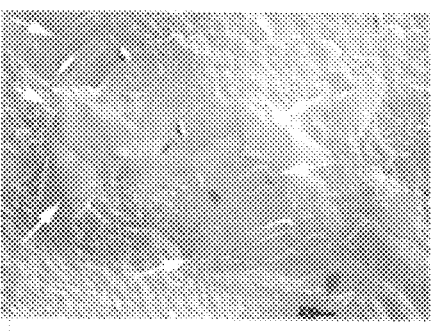
Figure 11G:
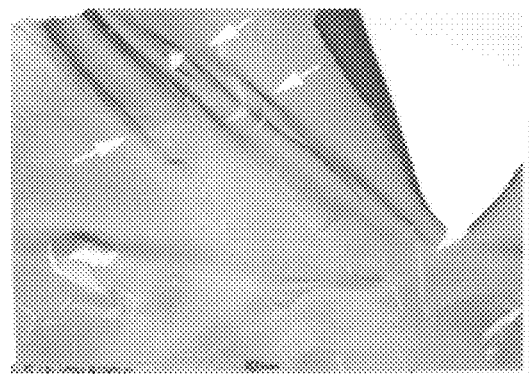
Figure 11H:
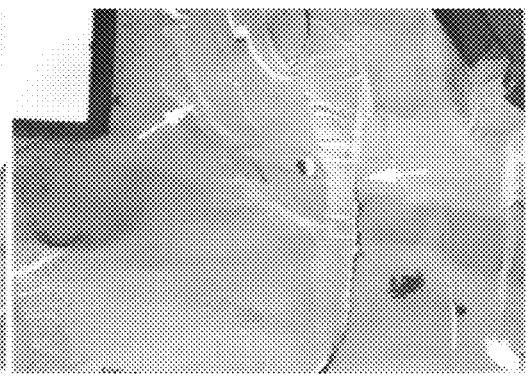
Figure 11I:
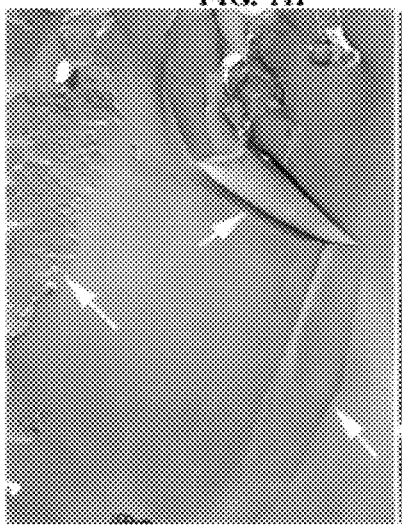
Figure 11J:

FIGS. 10A-B present a series of light microscopy photographs of samples of $C_{12}K$-$7\alpha_8$ (SEQ ID NO: 3) at a lipid to polymer ratio of 10:1 with POPE:TOCL 50:50 in FIG. 10A and with TOCL in FIG. 10B, showing few liposomes structures.

The morphology of the samples of different OAKs and different lipid mixtures could be classified into the following categories. The best cochleates seem to be those exhibiting crystal-like structures in the light microscopy images, with long needles protruding from a mass of aggregates, as can be seen in FIG. 6 and FIG. 9A, or a dense mass of elongated structures with few round liposomes (see, FIG. 6 middle image), all of which form large cochleates structures. Poor cochleate formers are notable in the light microscopy images as affording mostly liposomes as well as fewer structures altogether in the field of view, and smaller cochleates (see, FIGS. 8A-D and FIGS. 8A-D). Absence of cochleates is notable, as aggregates exhibit mostly round liposomes (see, FIG. 9E).

Binary lipid mixtures with TMCL, which has a high melting temperature (Tm of about 42° C.) as well as exhibiting solid phase polymorphism, in combination with DMPE, DMPG or POPE as well as DMPE:DMPG, had to be heated to 40-60° C. in order to hydrate the lipid film so as to form MLVs Likely as a result of this heating there was a loss in cochleate formation, preventing abundant assembly of structures or resulting in the opening up of some of the cochleates which did form.

The lipid to polymer ratio (L/P) used in this study was chosen to be 10:1 on the basis of freeze-fracture electron microscopy with the OAK $C_{12}K$-$7\alpha_8$ (SEQ ID NO: 3) in POPE:TOCL 75:25, indicating that cochleate formation proceeded in the order of L/P 20>10>5. Similarly, most of the mixtures with zwitterionic-anionic lipids were chosen to have 25 mol percent of anionic lipid, with the OAK $C_{12}K$-$7\alpha_8$ (SEQ ID NO: 3), in mixtures of POPE and TOCL with increasing negative charge the efficiency of cochleate formation proceeded in the order of POPE:TOCL 75:25> POPE:TOCL 50:50>TOCL (see, FIG. 10). POPE:TOCL 50:50 was a poor cochleate former (few structures mixed with abundance of liposomes) due to increased charge repulsion on the lipid headgroups, while TOCL alone produced an abundance of smaller liposomes as a result of the breakup of the MLVs (see, FIG. 10).

Table 5 presents the results of cochleate formation with different lipid mixtures of 1:10 lipid to polymer ratio, and a series of OAK polymers, indicated by their alternative denotations and SED ID Nos in parentheses. "Tm" denotes the melting temperature of the lipid bilayer afforded by the given lipid mixture. Some selected samples were further analyzed to confirm the results with freeze fracture electron microscopy for, as indicated in Table 5. Cochleate formation is defined as excellent (E) or above (E!), good (G), poor (P), or none (N) based on the aforementioned comparison, as well as on the abundance of cochleate structures observed in the light microscopy images. Lipid mixtures having a number in parenthesis are samples for which freeze-fracture electron microscopy analysis was conducted. Lipid mixtures having a "+" sign next to the number in parenthesis are samples which were confirmed by freeze-fracture electron microscopy as forming large cochleates with few vesicles and no inverted micellar ($H_{II}$) morphology (samples 2, 3 and 5), or smaller cochleate structures mixed with other morphologies (samples 0 and 4). Lipid mixtures which contain only anionic lipids are marked with "[A]". Sample 0 is the lipid/OAK system used and presented in Example 1 hereinabove.

TABLE 5

| Lipid Mixtures | Tm | $C_{12}K$-$5\alpha_8$ (1) | $C_{12}K$-$6\alpha_8$ (2) | $C_{12}K$-$7\alpha_8$ (3) | $C_{12}K$-$8\alpha_8$ (4) | $C_{12}K$-$9\alpha_8$ (5) | $C_{12}K$-$11\alpha_8$ (6) |
|---|---|---|---|---|---|---|---|
| POPE:TOCL 75:25 (0*) | 14-15 | G | G | G | G | G | G |
| DOPE:TOCL 75:25 | <0 | N | — | P | G | G | G |
| DMPE:TOCL 75:25 (2*) | 34 | P | — | E | E | E | G |
| DPPE:TOCL 75:25 (3*) | 60 | E | — | E | E | E | P |
| POPC:TOCL 75:25 (4) | <0 | P | — | P | — | N | P |
| POPE:DOPG 75:25 | 22 | G | — | N | N | G | P |
| POPE:DOPG:TOCL 80:15:5 | 18 | N | — | N | N | — | — |
| DMPE:DOPG 75:25 (5*) | 53 | E | G | E | G | E! | E |
| DMPC:TOCL 75:25 | 13-15 | N | — | N | — | N | — |
| POPG:TOCL 75:25 (1)[A] | <0 | P | — | G | — | P | N |
| DMPG:TOCL 75:25[A] | 15 | G | — | N | — | N | — |

As can be seen in Table 5, the ability to form cochleate structures with a particular lipid mixture was exhibited in the series comprising $C_{12}K$-$5\alpha_8$ (SEQ ID NO: 1), $C_{12}K$-$6\alpha_8$ (SEQ ID NO: 2), $C_{12}K$-$7\alpha_8$ (SEQ ID NO: 3), $C_{12}K$-$8\alpha_8$ (SEQ ID NO: 4), $C_{12}K$-$9\alpha_8$ (SEQ ID NO: 5) and $C_{12}K$-$11\alpha_8$ (SEQ ID NO: 6) the exemplary OAK polymers, with POPE:TOCL, DMPE:DOPG, or DMPC:TOCL. As can further be seen in Table 5, the lipid mixtures DMPE:TOCL 75:25, DPPE:TOCL 75:25 and DMPE:DOPG 75:25 were found to form larger cochleate and/or more abundant assemblies of cochleate across the series of the exemplary OAK polymers used for this experiment, as compared with mixtures of POPE:TOCL, POPG:TOCL, POPC:TOCL, DMPC:TOCL and POPE:DOPG (see, FIG. 6A-C).

Table 6 presents the results of cochleate formation with two lipid mixtures of 10:1 lipid to polymer ratio which gave the most frequent positive results with the series of OAK polymers presented in Table 5, and a series of OAK polymers, indicated by their alternative denotations and SED ID NOs. in parentheses, which represent specific structural and/or chemical characteristics. The exemplary OAK polymers are characterized by 8 lysine residues, but differ in hydrophobicity, represented by $C_{12}K$-$7\alpha_4$ (SEQ ID NO: 7) and $C_{12}K$-$7\alpha_{12}$ (SEQ ID NO: 9) as well as in charge, represented by $\alpha_{12}$-$7\alpha_8$ (SEQ ID NO: 8), with an extra amino group at the end of an acyl chain.

TABLE 6

| Lipid mixtures | $C_{12}K$-$7\alpha_4$ (7) | $\alpha_{12}$-$7\alpha_8$ (8) | $C_{12}K$-$7\alpha_{12}$ (9) |
|---|---|---|---|
| POPE:TOCL 75:25 | G-E | G-E | N |
| DMPE:TOCL75:25 | G | E | P |

As can be seen in both Table 5 and Table 6, cochleates were best obtained with the exemplary OAK $C_{12}K$-$9\alpha_8$ (SEQ ID NO: 5) in DMPE:DOPG 75:25, and the OAK polymers $C_{12}K$-$5\alpha_8$ (SEQ ID NO: 1) and $C_{12}K$-$11\alpha_8$ (SEQ ID NO: 6) were found to be in general the weakest cochleate formers. Nevertheless, all OAKs seem to be capable of forming cochleates to some extent, depending on the composition of the lipid mixture.

These observations are in accord with earlier studies on $Ca^{2+}$ and phosphatidylserine cochleate systems which indicated that greater acyl chain un-saturation, expressed in bend hydrocarbon chains leading to disrupted lipid bilayer, inhibited cochleate formation.

Freeze Fracture Electron Microscopy:

For freeze-fracture electron microscopy the samples were quenched in liquid nitrogen-cooled propane using the sandwich technique. Using this technique a cooling rate of 10,000 Kelvin per second is reached, avoiding artifacts caused by ice crystal formation. The cryo-fixed samples were stored in liquid nitrogen for less than 2 hours before processing. The fracturing and imaging process was carried out as described hereinabove.

FIGS. 11A-J present a series of freeze-fracture electron micrographs of $C_{12}K$-$7\alpha_8$ (SEQ ID NO: 3) with DMPE:TOCL 75:25 referred to as "sample 2" (FIGS. 11A-C), DPPE:TOCL 75:25 referred to as "sample 3" (FIGS. 11D-F), DMPE:DOPG 75:25 referred to as "sample 5" (FIGS. 11G-H), POPG:TOCL 75:25 referred to as "sample 1" (FIG. 11I) and POPC:TOCL 75:25 referred to as "sample 4" (FIG. 11J), at a molar ratio of 10:1 lipid to polymer, wherein the bar represents 100 nm on all electron micrographs, shadow direction is cast bottom to top and white arrows mark some cochleate structures.

Based on the elongated structures commonly observed in the freeze fracture electron micrographs, the selected samples that were studied were divided into two classes, samples of $C_{12}K$-$7\alpha_8$ (SEQ ID NO: 3) with DMPE:TOCL 75:25 (FIGS. 11A-C), with DPPE:TOCL 75:25 (FIGS. 11D-F) or with DMPE:DOPG 75:25 (FIGS. 11G-H) display larger elongated structures up to 9 µm in length. These bilayer structures are assumed to be pre-formed cochleates or true cochleate structures. In this group of samples only very few vesicles and few non-cochleate structures are observed. In comparison, POPG:TOCL 75:25 (FIG. 11I) or POPC:TOCL 75:25 (FIG.

11J) at a 10:1 molar ratio of lipid to polymer, exhibited smaller, around 1 μm, elongated structures somewhat similar to those found in the samples with POPE:TOCL 75:25 with the OAK $C_{12}K$-$7\alpha_8$ (SEQ ID NO: 3).

Although freeze-fracture images are of higher resolution and more detailed than those of light microscopy, the morphology of the OAK/lipid samples determined by freeze fracture electron microscopy (FIGS. 11A-J) agree with the observations using light microscopy (see, Table 5) for the samples that were studied by both imaging methods. Thus $C_{12}K$-$7\alpha_8$ (SEQ ID NO: 3) weakly promoted cochleate formation with mixtures of POPC:TOCL (75:25) or POPG:TOCL (75:25) and strongly promoted the formation of large cochleates with mixtures of DMPE:TOCL (75:25), DPPE:TOCL (75:25) or DMPE:DOPG (75:25).

The ranges of cochleate lengths observed in the micrographs are presented in Table 7.

TABLE 7

| Lipid mixtures with $C_{12}K$-$7\alpha_8$ (SEQ ID NO: 3) | Pre-formed and fully formed cochleate Length (μm) |
|---|---|
| POPG:TOCL 75:25 | 1.5 ... 2.5 ... 3.1 |
| DMPE:TOCL 75:25 | 2.3 ... 5.5 ... 9.1 |
| DPPE:TOCL 75:25 | 0.7 ... 2.1 ... 5.2 |
| POPC:TOCL 75:25 | (1.8) |
| DMPE:DOPG 75:25 | 1.0 ... 3.6 ... 5.7 |

As can be seen in Table 7, the larger cochleate structures were obtained from lipid mixture characterized by the highest Tm in all the lipid mixtures used in this example, namely DMPE:TOCL 75:25 having Tm of 34° C., DPPE:TOCL 75:25 having Tm of 60° C., and DMPE:DOPG 75:25 having Tm of 34° C., DPPE:TOCL 75:25 having Tm of 53° C. The size of the observed cochleates, other than facilitating their identification, further indicate their stability and tendency of the composition to form cochleate structures.

Structure-Function Analysis:

One of the observations in the experiments presented hereinabove is that cochleates are formed without the presence of divalent cations such as $Ca^{2+}$. The cochleate structures observed by light microscopy with OAK-lipid mixtures can be identified by comparing microscopy images with those formed with compounds in the presence of PS and $Ca^{2+}$. Without being bound by any particular theory, the results suggest that the polycationic OAKs are acting the role of divalent cations in bridging lipid molecules. The proposed mechanism that the structures that form between PS and $Ca^{2+}$ proceeds by fusion of aggregated vesicles into large cochleates has extended to OAK-lipid cochleate structures as well.

The balance between charge and hydrophobicity of OAK plays a role in achieving cochleates, as can be seen in Table 6. Increasing the chain length of the ω-amino fatty acid from $C_{12}K$-$7\alpha_4$ (SEQ ID NO: 7) to $C_{12}K$-$7\alpha_8$ (SEQ ID NO: 3) improved cochleate formation, but further increasing chain length of the ω-amino fatty acid to $C_{12}K$-$7\alpha_{12}$ (SEQ ID NO: 9) resulted in the opposite effect. This biphasic behavior is assumed to be a consequence of increased hydrophobicity favoring cochleate formation, but extending the distance between cationic groups presumably disfavors it. A chain length of the ω-amino fatty acid of 6-10 carbon atoms is assumed to increase the probability of cochleate structure formation, according to some embodiments of the present invention. A shorter carbon chain is considered to be too short to effect the required hydrophobicity and favorable interaction with the lipids, which a longer carbon chain is assumed to drive the OAK into intra-folding and homo-aggregation.

The N-terminus of the OAK also plays a part in driving the system with lipids into forming cochleates, assuming that the long carbon chain at the N-terminus interacts with the lipid bilayer and anchors the OAK therein.

Increasing the positive charge of the lipid/OAK system decreases cochleate formation due to electrostatic repulsion, however increased negative charge on the lipid part facilitates the extent and strength of binding of the OAKs to the lipid bilayer. However, in several cases increased negative charge on the lipid lead to decreased cochleate formation (see, FIGS. 10A-B). Although POPG:TOCL 75:25 does not form cochleates, DMPG:TOCL 75:25 does form these structures (see, data obtained for the OAK $C_{12}K$-$5\alpha_8$ (SEQ ID NO: 1). It is noted that this OAK forms cochleates with the more highly negatively charged lipid mixture, even though the OAK itself is less positively charged. In addition, the formation of cochleates does not seem to require the clustering of anionic lipids in the presence of zwitterionic lipids, as has been found for several antimicrobial agents, since a mixture composed only of anionic lipids can form cochleates with OAKs. It should be noted that this does not negate the possibility that there is segregation of the two anionic lipids that could facilitate cochleate formation.

Dehydration of the membrane interface appears to play a role in facilitating the coiling up of the bilayer when bridged by cationic molecules. Thus, PC is more hydrated than PE and has a lesser tendency to form cochleates in these lipid mixtures. Similarly CL is internally hydrogen bonded; an H-bonded ring structure formed between the two phosphates and the central OH group of CL makes for a tighter packing of the four hydrophobic acyl chains on each molecule. PE and PG have hydrogen bonding among the lipid headgroup but not to water. PE and CL have particularly small headgroups relative to their acyl chains and are poorly hydrated. In PG besides hydrogen bonding, the headgroup has ionic bonds and coordination bonds both in the anhydrous crystal state and in the hydrated gel state forming a tight network, although this H-bonding network would be weaker in the liquid crystalline state than that of CL or PE. It is therefore suggested that a factor contributing to the ability to form cochleates with OAKs is a less hydrated membrane interface resulting from a stable hydrogen bonding network among the headgroups of these lipids.

Inter-related with dehydration is the melting temperature (Tm). Lipids with a more dehydrated interface tend to have a higher melting temperature. The PE headgroup also forms a compact rigid network of hydrogen bonds at the bilayer surface, giving it higher Tm values than PC. It has been shown that in the case of cochleates formation from phosphatidylserine and Ca2+, the divalent cation markedly raises the melting temperature of the lipid. With regard to the lipid mixtures with OAK polymers, there is a correlation between the melting temperature and the tendency to form cochleates. Thus, the presence of DPPE or DMPE with an anionic lipid results in increased cochleate formation than does POPE, which is better in forming cochleates than DOPE, the lowest melting of the PE lipids used. It appears that the presence of a higher melting lipid contributes to the tendency to form cochleates.

In summary, cochleate structure formation has been shown between several different antimicrobial OAK polymers and various lipid mixtures, particularly lipid mixtures which have not been shown to form cochleates hitherto. Cochleate structures have been formed in the absence of divalent cations, as well as in the presence of lipid mixtures whose composition mimic those of bacterial cytoplasmic membranes. Dehydration plays a major role in the lipid mixtures favoring headgroups composed of PE, CL, or PG, and the gel state optimizes cochleate formation with regard to their size and abundance.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising a cochleate and a polymer encapsulated in said cochleate, said cochleate being formed from a mixture of at least two phospholipids characterized by a melting temperature higher than 10° C., wherein at least one of said phospholipids is a zwitterionic phosphatidylethanolamine and at least another phospholipid is an anionic diphosphatidylglycerol, and wherein said polymer comprises from 2 to 12 combined units and an N-terminus unit attached to one-another via a peptide bond, each of said combined units consisting of an ω-amino-fatty acid moiety attached via a peptide bond to a lysine residue, each of said ω-amino-fatty acid moiety independently exhibits a hydrocarbon chain of 4-12 carbon atoms, and said N-terminus unit being selected from the group consisting of a lysine residue having a $NC_{10-16}$ fatty acid moiety attached thereto and a lysine residue having a $C_{10-16}$ fatty acid moiety attached thereto.

2. The composition-of-matter of claim 1, being substantially devoid of multivalent metal cations.

3. The composition-of-matter of claim 1, wherein a net positive charge of said polymer ranges from 6 to 12.

4. The composition-of-matter of claim 3, wherein said net positive charge of said polymer ranges from 8 to 10.

5. The composition-of-matter of claim 1, wherein each of said ω-amino fatty acid moieties is independently selected from the group consisting of 4-amino-butyric acid, 6-aminocaproic acid, 8-amino-caprylic acid, 10-amino-capric acid and 12-amino-lauric acid.

6. The composition-of-matter of claim 1, wherein each of said ω-amino fatty acid moieties is 8-amino caprylic acid.

7. The composition-of-matter of claim 1, wherein said polymer has the general Formula I:

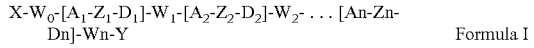

$$X-W_0-[A_1-Z_1-D_1]-W_1-[A_2-Z_2-D_2]-W_2- \ldots [A_n-Z_n-D_n]-W_n-Y \qquad \text{Formula I}$$

wherein:

n is an integer from 2 to 50;

$A_1, A_2, \ldots, A_n$ are each independently a lysine residue;

$D_1, D_2, \ldots, D_n$ are each independently said w-amino-fatty acid moiety or absent, provided that at least 2 to 12 of said $D_1, D_2, \ldots, D_n$ is said ω-amino-fatty acid moiety;

$Z_1, Z_2, \ldots, Z_n$ and $W_0, W_1, W_2, \ldots, W_n$ are each a peptide bond or absent;

Y is said N-terminus unit; and

X is selected from the group consisting of hydrogen, amine, amide, a positively charged amino acid residue, an w-amino-fatty acid moiety and a fatty acid moiety, or absent.

8. The composition-of-matter of claim 1, wherein said polymer is selected from the group consisting of $C_{12}K(NC_8K)_5NH_2$ (SEQ ID NO: 1), $C_{12}K(NC_8K)_6NH_2$ (SEQ ID NO: 2), $C_{12}K(NC_8K)_7NH_2$ (SEQ ID NO: 3), $C_{12}K(NC_8K)_8NH_2$ (SEQ ID NO: 4), $C_{12}K(NC_8K)_9NH_2$ (SEQ ID NO: 5), $C_{12}K(NC_8K)_{11}NH_2$ (SEQ ID NO: 6), $C_{12}K(NC_4K)_7NH_2$ (SEQ ID NO: 7), $NC_{12}K(NC_8K)_7NH_2$ (SEQ ID NO: 8) and $C_{12}K(NC_{12}K)_7NH_2$ (SEQ ID NO: 9).

9. The composition-of-matter of claim 1, wherein said mixture is characterized by a melting temperature that ranges from 15 to 45° C.

10. The composition-of-matter of claim 1, wherein at least one of said at least two phospholipids in said mixture is selected from the group consisting of POPE, DPPE, DOPE, DMPE and DMPC.

11. The composition-of-matter of claim 10, wherein another of said at least two phospholipids in said mixture is selected from the group consisting of TOCL and TMCL.

12. The composition-of-matter of claim 1, wherein said mixture is essentially devoid of phosphatidylserine.

13. The composition-of-matter of claim 1, further comprising a bioactive agent co-encapsulated in said cochleate.

14. The composition-of-matter of claim 13, wherein said bioactive agent is an antibiotic agent.

15. A pharmaceutical composition comprising the composition-of-matter of claim 1 and a pharmaceutically acceptable carrier.

16. The pharmaceutical composition of claim 15, packaged in a packaging material and identified, in or on said packaging material, for use in the treatment of a medical condition treatable by said polymer.

17. The pharmaceutical composition of claim 15, wherein the composition-of-matter further comprises a bioactive agent co-encapsulated in said cochleate.

18. The pharmaceutical composition of claim 17, being packaged in a packaging material and identified, in or on said packaging material, for use in a systemic or local delivery of said bioactive agent to a bodily site of a subject in need thereof.

19. The pharmaceutical composition of claim 17, wherein said bioactive agent is an anticancerous agent, the composition being identified for use in the treatment of cancer.

20. The pharmaceutical composition of claim 17, wherein said bioactive agent is an antibiotic, the composition being packaged in a packaging material and identified, in or on said packaging material, for use in treating a medical condition associated with a pathogenic microorganism.

21. The pharmaceutical composition of claim 20, wherein said pathogenic microorganism is a resistant microorganism, the composition being further identified for sensitizing or re-sensitizing said resistant microorganism to said antibiotic agent.

22. A method of treating a medical condition associated with a pathogenic microorganism, the method comprising administering to a subject in need thereof a therapeutically effective amount of the composition-of-matter of claim 1.

23. The method of claim 22, wherein said pathogenic microorganism is a resistant microorganism, the method being for sensitizing or re-sensitizing said microorganism to an antibiotic agent.

24. A method of delivering a bioactive agent to a bodily site of a subject in need thereof, the method comprising administering to the subject the composition-of-matter of claim 13.

25. The method of claim 24, wherein said bioactive agent is an anticancerous agent, the method being for the treatment of cancer.

26. The method of claim 24, wherein said bioactive agent is an antibiotic, the method being for treating a medical condition associated with a pathogenic microorganism.

27. The method of claim 26, wherein said pathogenic microorganism is a resistant microorganism, the method for sensitizing or re-sensitizing said resistant microorganism to said antibiotic agent.

28. A process of preparing the composition-of-matter of claim 1, the process comprising:

providing a dehydrated film of said mixture; and hydrating said film with an aqueous solution of said polymer, thereby obtaining the composition-of-matter.

29. The process of claim 28, wherein said mixture is essentially devoid of phosphatidylserine.

30. The process of claim 28, performed essentially in the absence of a multivalent metal cation.

31. A polymer having the formula $C_{12}K(NC_8K)_{11}NH_2$ (SEQ ID NO: 6).

* * * * *